United States Patent [19]

Hirata et al.

[11] 4,291,164

[45] Sep. 22, 1981

[54] CEPHALOSPORIN ANALOGS AND METHODS FOR PRODUCTION THEREOF

[75] Inventors: Tadashi Hirata, Yokohama; Takehiro Ogasa, Machida; Hiromitsu Saito, Machida; Nobuhiro Nakamizo, Machida, all of Japan

[73] Assignee: Kyowa Hakko Kogyo Co., Ltd., Tokyo, Japan

[21] Appl. No.: 23,645

[22] Filed: Mar. 23, 1979

[30] Foreign Application Priority Data

Mar. 20, 1978 [JP] Japan ................................ 53-34696
Oct. 4, 1978 [JP] Japan ................................ 53-122404
Oct. 28, 1978 [JP] Japan ................................ 53-133072
Dec. 26, 1978 [JP] Japan ................................ 53-162005
Jan. 27, 1979 [JP] Japan ................................ 54-8408

[51] Int. Cl.$^3$ .............................................. C07D 221/02
[52] U.S. Cl. .................................. 546/183; 424/244; 546/183
[58] Field of Search .......................................... 546/183

[56] References Cited

FOREIGN PATENT DOCUMENTS 2524443 12/1975 Fed. Rep. of Germany ...... 546/183

Primary Examiner—Donald G. Daus
Assistant Examiner—D. B. Springer
Attorney, Agent, or Firm—Fitzpatrick, Cella, Harper & Scinto

[57] ABSTRACT

Novel cephalosporin analogs are disclosed which are useful as intermediates in the production of other compounds having antibacterial activity. Methods for producing the compounds are also disclosed.

3 Claims, No Drawings

CEPHALOSPORIN ANALOGS AND METHODS FOR PRODUCTION THEREOF

BACKGROUND OF THE INVENTION

The present invention relates to novel cephalosporin analogs and more specifically to new carbacephem compounds which differ from cephalosporin by having carbon atom instead of sulphur atom in dihydrothiazine ring. In the Journal of the American Chemical Society, 96, 7584 (1974) and J. Med. Chem., 20, 551 (177) certain carbacephems with substituted methyl groups at the C-3 position such as (±)-1-carbacephalotin represented by the formula:

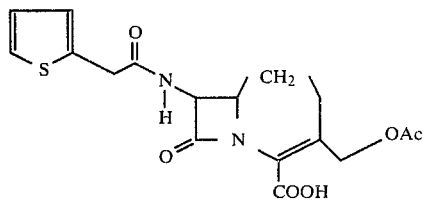

are disclosed as having antibacterial activity. Nevertheless as microorganism populations develop immunity to existing antibiotics new antibacterial compounds are in demand. To this end, as is disclosed hereinafter, novel carbacephems with hydrogen atom at C-3 position have been synthesized which are useful as intermediates in the preparation of unexpectedly high antibacterial compounds.

SUMMARY OF THE INVENTION

In accordance with the present invention, novel carbacephem compounds, i.e. cephalosporin analogs, are synthesized. The numbering system shown in the following formula is used hereinafter.

Broadly, the present invention relates to cephalosporin analogs represented by the formula:

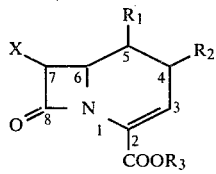

wherein X represents an amino group, azido group or phthalylimino group; $R_1$ represents a hydrogen atom, a halo group, hydroxy group, a lower alkoxy group, an aryloxy group, an aralkyloxy group, an acyloxy group, a sulfonyloxy group, a lower alkylthio group, an arylthio group, an aralkylthio group, a lower alkylsulfinyl group, an arylsulfinyl group, an aralkylsulfinyl group, a sulfonium group represented by the general formula $—S^+R_4R_5$ (wherein $R_4$ and $R_5$ may be the same or different and represent a lower alkyl group, an aryl group or an aralkyl group), a lower alkylsulfonyl group, an arylsulfonyl group, an aralkylsulfonyl group, a quarternary ammonium group represented by the general formula $N^+R_6R_7R_8$ (wherein $R_6$, $R_7$ and $R_8$ may be the same or different and represent a lower alkyl group, an aryl group or an aralkyl group), an arylselenyl group or an arylseleninyl group; $R_2$ represents a group as defined for $R_1$ above or represents a lower alkyl group, a lower alkyl group substituted with one or more halogens, an azido group, a nitrile group or an amino group represented by the general formula $NR_9R_{10}$ wherein $R_9$ and $R_{10}$ may be the same or different and represent a hydrogen atom, a lower alkyl, aryl or aralkyl group; and $R_3$ represents a hydrogen atom or a substituted or unsubstituted alkyl, aryl, aralkyl or silyl group.

Included in the composition of matter aspect of the invention are the salts of the compounds defined above.

The invention also pertains to the processes for the synthetic production of the cephalosporin analogs of the invention.

DESCRIPTION OF THE INVENTION

This invention relates to compounds represented by the general formula [I]

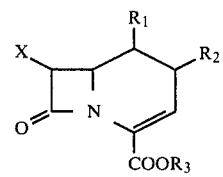

wherein X represents an amino group, azido group or phthalylimino group; $R_1$ represents a hydrogen atom, a halo group, hydroxy group, a lower alkoxy group, an aryloxy group, an aralkyloxy group, an acyloxy group, a sulfonyloxy group, a lower alkylthio group, an arylthio group, an aralkylthio group, a lower alkylsulfinyl group, an arylsulfinyl group, an aralkylsulfinyl group, a sulfonium group represented by the general formula $—S^+R_4R_5$ (wherein $R_4$ and $R_5$ may be the same or different and represent a lower alkyl group, an aryl group or an aralkyl group), a lower alkylsulfonyl group, an arylsulfonyl group, an aralkylsulfonyl group, a quarternary ammonium group represented by the general formula $N^+R_6R_7R_8$ (wherein $R_6$, $R_7$ and $R_8$ may be the same or different and represent a lower alkyl group, an aryl group or an aralkyl group), an arylselenyl group, or an aryleseleninyl group; $R_2$ represents a group as defined for $R_1$ or represents a lower alkyl group, a lower alkyl group substituted with one or more halogens, an azido group, a nitrile group or an amino group represented by the general formula $NR_9R_{10}$ wherein $R_9$ and $R_{10}$ may be the same or different and represent a hydrogen atom, a lower alkyl group, an aryl group or an aralkyl group; and $R_3$ represents, a hydrogen atom or a substituted or unsubstituted alkyl, aryl, aralkyl or silyl group.

In particular, the present invention relates to novel cephalosporin analogs represented by the general formula [I-1].

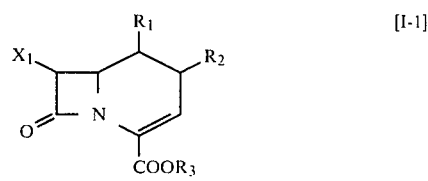

where $X_1$ represents an azido group or phthalylimino group, $R_1$, $R_2$ and $R_3$ have the same significance as defined above; and also compounds represented by the general formula [I-2].

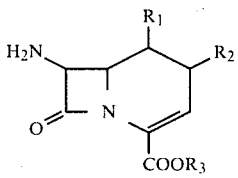

[I-2]

wherein $R_1$, $R_2$, and $R_3$ have the same significance as defined above; and the salt thereof.

In a broad aspect of the invention as represented by the above general formula [I], $R_1$ and $R_2$ are more specifically as follows:

As a halo group the appropriate halogen atom is fluorine, chlorine, bromine, or iodine.

As a lower alkoxy group, an alkoxy group having 1 to 5 carbon atoms, such as a methoxy group, ethoxy group, a straight-chain or branched propoxy group or butoxy group, and the like are appropriate.

As an aryloxy group, a phenoxy group or a phenoxy group having a substituent such as methyl group, methoxy group, nitro group, and the like, at the ortho, meta or para position is appropriate.

As an aralkyloxy group, an aralkyloxy group having 7 to 10 carbon atoms such as a benzyloxy group, phenethyloxy group, and the like are appropriate.

As an acyloxy group, a substituted or unsubstituted acyloxy group having 1 to 5 carbon atoms such as an acetoxy group, propionyloxy group, trifluoroacetoxy group, etc., a benzoxy group or a benzoxy group having a substituent such as a methyl group, methoxy group, nitro group, etc. at the ortho, meta or para position is appropriate.

As a sulfonyloxy group, an alkylsulfonyloxy group having 1 to 5 carbon atoms such as a methyl group, ethyl group, propyl group, butyl group, and the like or an arylsulfonyloxy group having 6 to 8 carbon atoms such as a benzenesulfonyloxy group, toluenesulfonyloxy group, are appropriate.

As a lower alkylthio group, an alkylthio group having 1 to 5 carbon atoms such as a methyl group, ethyl group, straight-chain or branched propyl or butyl group, and the like are appropriate.

As an arylthio group, an arylthio group having 6 to 10 carbon atoms such a phenylthio group, methoxyphenylthio group, tolylthio group, etc. are appropriate.

As an aralkylthio group, an aralkylthio group having 7 to 10 carbon atoms such as a benzylthio group, methoxybenzylthio group, phenethylthio group, etc. are appropriate.

As a lower alkylsulfinyl group, an arylsulfinyl group and aralkylsulfinyl group, sulfoxides corresponding to the lower alkylthio group, arylthio group and aralkylthio group described above are appropriate.

As a lower alkylsulfonyl group, an arylsulfonyl group and aralkylsulfonyl group, sulfones corresponding to the lower alkylthio group, arylthio group and aralkylthio group described above are appropriate.

As a arylselenyl group, a phenylselenyl group, o-nitrophenylselenyl group, etc. are appropriate.

As an arylseleninyl group, seleneoxides corresponding to the arylselenyl group described above are appropriate.

As a lower alkyl group, an alkyl group having 1 to 5 carbon atoms such as a methyl group, ethyl group, straight-chain or branched propyl or butyl group, and the like are appropriate.

As a lower alkyl group substituted with halogen(s), a lower alkyl group substituted with fluorine, chlorine, bromine or iodine is exemplary.

As an aryl group, a phenyl group or an aryl group having 6 to 10 carbon atoms with or without such substituents as a methyl group, methoxy group, nitro group, and the like at the ortho, meta or para position are appropriate.

As an aralkyl group, an aralkyl group having 7 to 15 carbon atoms such as benzyl group, phenethyl group, methoxybenzyl group, and the like are appropriate.

As an ester represented by —$COOR_3$, an ester generally employed in the field of the synthetic chemistry of penicillins or cephalosporins is suitable. The ester is preferably selected from those groups easily converted to a carboxy group without decomposition of substituents and functional groups of carbacephems under suitable conditions. In the general formula [I], $R_3$ represents an alkyl group having 1 to 5 carbon atoms such as a methyl group, ethyl group, n-propyl group, isopropyl group, n-butyl group, isobutyl group, t-butyl group, and the like, a halogenated alkyl group having 1 to 5 carbon atoms such as a chloromethyl group, 2,2,2-trichloroethyl group, 2,2,2-tetrafluoroethyl group, etc., an arylmethyl group having 7 to 20 carbon atoms such as a benzyl group, diphenylmethyl group, triphenylmethyl group, etc., an arylmethyl group having 7 to 20 carbon atoms and having a methoxy group, nitro group, etc. on the phenyl ring and a substituted silyl group such as trimethylsilyl group, triphenylsilyl group.

Compounds of the present invention represented by the general formula [I] include all stereoisomers at the 5, 4 (when $R_1$ and $R_2$ are not hydrogen), 6, and 7 positions.

As used hereinafter, compounds represented by the general formula [I], [II], etc., are identified as Compound [I], Compound [II], etc., respectively.

Compound [I] can be produced according to Processes I to VIII set forth below, i.e. Compound [I-1] is produced according to Process(es) I, II, III, IV, V, VI and/or VII and Compound [I-2] is produced according to Process(es) VII and/or VIII.

Process I

Compound [Ia] represented by the general formula [I] wherein X is an azido group or phthalylimino group, $R_1$ is a hydrogen atom, $R_2$ is hydrogen atom or a lower alkyl group and $R_3$ is a substituted or unsubstituted alkyl, aryl or aralkyl group can be produced by the method illustrated in the following Flow Sheet I.

Flow Sheet I

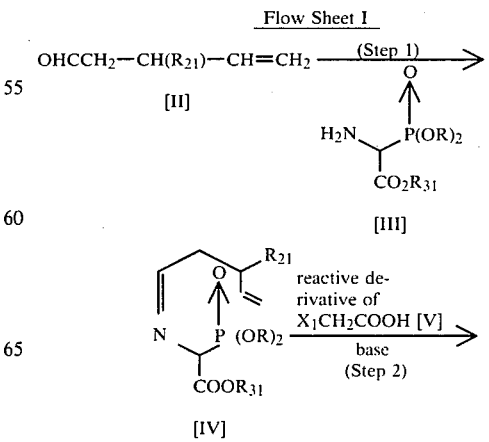

-continued
Flow Sheet I

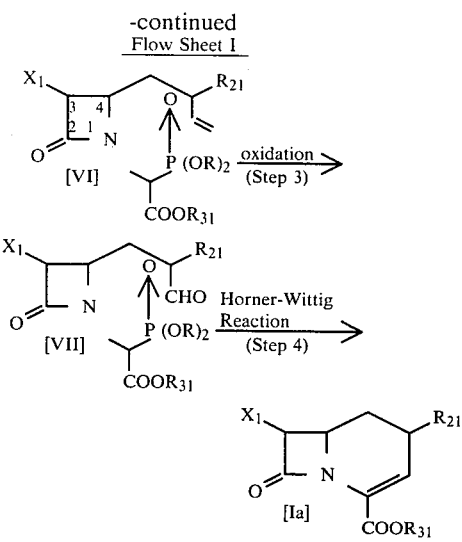

In the compounds produced by the steps set forth in Flow Sheet I, $X_1$ represents an azido group or phthalylimine-group, $R_{21}$ represents a hydrogen atom or a lower alkyl group, $R_{31}$ represents a substituted or unsubstituted alkyl, aryl or aralkyl group and the reactive derivative of $X_1CH_2COOH$ represents an acid halide, an acid anhydride, a mixed acid anhydride of $X_1CH_2COOH$ or a functionally equivalent derivative thereof and R represents a lower alkyl group.

Compound [II], the starting compound, is a known compound and is generally synthesized by the Claisen Rearrangement of a substituted allylvinylether represented by $CH_2=CHO—CH_2.CH=CH—R_{21}$ wherein $R_{21}$ has the same significance as defined above [Organic Reactions Vol. 22, 1, 1975 and Journal Of The Chemical Society, 4092 (1961)].

Compound [III] is a known compound and can be produced by the method described in German Offenlegungsschrift No. 2365456. Compound [III] represented by the general formula [III] wherein $R_{31}$ is $^tBu$ can be produced by a method wherein dialkylphosphonoacetate is nitrosified and the obtained oxime is reduced in conventional manner.

The reactions set forth in Flow Sheet I can be carried out under known reaction conditions; specific examples of which are outlined below.

Step 1

Compounds represented by the general formula [IV]

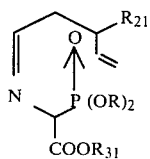

wherein R, $R_{21}$, and $R_{31}$ have the same significance as defined above, are produced by dehydrating condensation of Compound [II] and Compound [III]. The condensation is usually carried out in a non-aqueous solvent which does not affect the reaction. Compound [II] is preferably used in an amount of 1 to 2 equivalents to Compounds [III].

The solvent is selected from halogenated hydrocarbons such as methylene chloride, chloroform, carbon tetrachloride, dichloroethane, etc., aromatic hydrocarbons such as benzene, toluene, xylene, etc., aliphatic hydrocarbons such as n-hexane, cyclohexane, petroleum ether, ligroin, etc., ethers such as diethyl ether, tetrahydrofuran, dimethylcellosolve, etc., esters such as methyl acetate, ethyl acetate, etc., amides such as dimethyl acetoamide, dimethylformamide, etc., acetonitrile, dimethylsulfoxide, hexamethylphosphoryltriamide, etc. Mixtures thereof are preferably used. Since the reaction is accompanied by water as a by-product, the solvent is preferably used in an anhydrous condition. Furthermore, it is preferable to remove the water to enhance the reaction and increase the yield of the desired compound. Therefore, dehydration is preferably carried out (1) in the presence of a suitable dehydrating agent such as a molecular sieve, anhydrous magnesium sulfate, anhydrous sodium sulfate, and the like; (2) by passing the reaction solution into a column packed with the said dehydrating agents; and/or (3) by removing formed water azeotropically out of the reaction system.

The reaction is carried out with cooling or heating under reflux, preferably at a temperature of $-20°$ to $50°$ C., generally for 30 minutes to 5 hours.

After the completion of the reaction, the reaction mixture can be used in the next reaction as it is or after removing solids by filtration. Alternatively, the filtrate is concentrated under reduced pressure and the solvent in the concentrate is removed in vacuo. Thereafter the residue can be used in the next reaction.

Step 2

Compound [VI] represented by the general formula [VI]

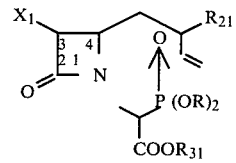

wherein $X_1$, R, $R_{21}$, and $R_{31}$ have the same significance as defined above, is produced by reacting Compound IV obtained in Step 1 with an reactive derivative of $X_1CH_2CO_2H$ represented by the general formula [V] in the presence of a base in a non-aqueous solvent to form a $\beta$-lactam ring.

As the reactive derivative, acid halides, acid anhydrides, mixed acid anhydrides, active esters, and the like are suitable.

The reaction is carried out by gradually adding Compound [V] or a solution containing Compound [V] into a solution containing Compound [IV] and a base. The reaction may also be carried out by adding the base or a solution containing the base into a solution containing Compound [IV] and Compound [V].

As the base, an organic base such as triethylamine, N-methylmorpholine, pyridine, etc. is used.

The base and Compound [V] are used in an equivalent amount or excess, preferably 1 to 2 equivalents, to Compound [IV].

As the solvent, any solvent which does not affect the reaction, preferably the solvent used in Step 1, is used.

The reaction is carried out with cooling or heating under reflux, preferably at a temperature of $-20°$ to $50°$ C. generally for 1 to 7 hours.

The addition of the base and Compound [V] is carried out in 30 minutes to 5 hours. After the addition, the reaction is continued for 15 minutes to 2 hours.

After completion of the reaction, isolation of the desired compound is carried out in conventional manner, for example, the reaction solution is washed successively with an acid, an alkali, and water or vice versa, dried and the solvent is removed under reduced pressure to obtain a residue which is then subjected to column chromatography, if necessary.

Step 3

Compound [VII] represented by the general formula [VII]

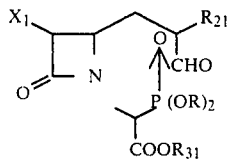

wherein $X_1$, R, $R_{21}$, and $R_{31}$ have the same significance as defined above, is produced by oxidation of Compound [VI] obtained in Step 2.

The following four oxidation methods are suitable for oxidation of Compound [VI].

(1) Lemieux-Johnson's Method

Compound [VII] is produced by the oxidative cleavage of the double bond of Compound [VI] with osmium tetroxide and sodium periodate in a solvent.

In the reaction, osmium tetroxide is used in the amount of 0.005 to 0.5 molar equivalent, preferably 0.01 to 0.1 molar equivalent, to Compound [VI] and sodium periodate is used in an amount of 1 to 5 molar equivalents, preferably 2 to 3 molar equivalents, to Compound [VI].

As the solvent, any solvent which does not affect the reaction, preferably a mixed solvent of water and dioxane, tetrahydrofuran, acetone, ether, methanol or acetic acid, may be used.

The reaction is carried out generally at a temperature of 0° to 50° C. for 30 minutes to 2 hours.

(2) Lemieux-Von Rudloff's Method

Compound [VII] is produced by the oxidative cleavage of the double bond of Compound [VI] with sodium periodate and potassium permanganate.

In the reaction, sodium periodate is used in an amount of 1 to 10 molar equivalents, preferably 2 to 4 molar equivalents, to Compound [VI] and potassium permanganate is used in an amount of 0.01 to 0.5 molar equivalent, preferably 0.05 to 0.3 molar equivalent, to Compound [VI].

As the solvent, the same solvent as used in Method (1) is preferably used.

The reaction is generally carried out at a temperature of 0° to 50° C., preferably 5° to 25° C. for 30 minutes to 48 hours, preferably 2 to 12 hours.

(3) Ozone Method

Compound [VII] is produced from Compound [VI] by using ozone. That is, Compound [VI] is converted to the ozonide thereof with ozone and the ozonide is decomposed to make Compound [VII].

In the reaction, ozone gas is passed through the reaction mixture until the double bond in Compound [VI] is removed.

As the solvent, any solvent which does not affect the reaction, preferably ethylacetate, benzene, chloroform, methylenechloride, methanol, ethanol, acetic acid, etc., are used alone or in combination.

The reaction is carried out generally at a temperature of −80° to 0° C., preferably −80° to −40° C. for a few minutes to several hours.

The ozonide formed is decomposed with zinc-acetic acid, dimethylsulfide, potassium iodide, stannous chloride to obtain Compound [VII]. The reagents are generally used in excess to insure completion of the reaction.

(4) Diol Method

Compound [VII] is produced in a conventional manner, for example by the use of sodium periodate and aqueous sulfuric acid, via a diol compound, Compound [VI'], represented by the general formula [VI']

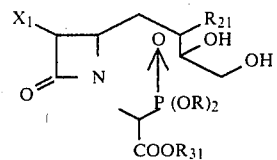

wherein $X_1$, R, $R_{21}$, and $R_{31}$ have the same significance as defined above.

The diol compound, Compound [VI'], can be prepared according to conventional manner whereby a diol compound is synthesized from an olefin compound. As a typical example, an olefin compound is treated with osmium tetroxide and a chlorate. In the reaction, osmium tetroxide is used in an amount of 0.05 to 0.5 molar equivalent, preferably 0.01 to 0.1 molar equivalent, to Compound [VI] and the chlorate is used in an amount of 1 to 5 molar equivalents preferably 2 to 3 molar equivalents to Compound [VI]. As a chlorate, sodium chlorate, potassium chlorate, silver chlorate, barium chlorate, etc. are preferably used. As a solvent, any solvent which does not affect the reaction, and preferably a mixed solvent of water and dioxane, tetrahydrofuran, ether, ethanol, or the like is used.

The reaction is generally carried out at a temperature of 0° to 80° C., preferably 10° to 50° C., for 1 to 48 hours, preferably 10 to 20 hrs.

The diol compound, Compound [VI'], may also be prepared via an epoxy compound. As epoxidating agents, any agent which does not affect the other functional groups may be used. Preferred agents are organic peracids such as metachloroperbenzoate, peracetate, etc. The epoxy compound obtained is converted into a diol compound in conventional manner.

Step 4

Compound [Ia] represented by the general formula [Ia]

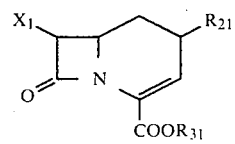

wherein $X_1$, $R_{21}$, and $R_{31}$ have the same significance as defined above, is produced by the condensation reaction of Compound [VII] obtained in Step 3 in a nonaqueous solvent and in the presence of a base to form a ring. The reaction is generally called a Horner-Wittig Reaction which is disclosed in *Organic Reactions* Vol. 25, p. 73, 1977, published by John Wiley and Sons.

A suitable base may be sodium hydride, potassium hydride, sodium methoxide, sodium ethoxide, potassium tertbutoxide, sodium hydroxide, potassium hydroxide, potassium carbonate, and the like. The base is generally used in an amount of 1 to 1.2 molar equivalents to Compound [VII].

As the solvent, any solvent which does not affect the reaction, preferably dimethoxyethane, dimethylformamide, dimethylsulfoxide, hexamethylphosphoryltriamide, tetrahydrofuran, dioxane, ethylether, acetonitrile, benzene, toluene, ethanol, tert-butanol, etc. are used alone or in combination.

The reaction is carried out with cooling or heating, generally at a temperature of 0° to 50° C., and preferably 0° to 25° C. for a few minutes to several hours.

Isolation of the desired compound is carried out by conventional means. For example, after completion of the reaction, acetic acid in an equivalent or excess amount to the base used is added to the reaction mixture. After a part of the solvent is distilled off, the reaction solution is poured into an ice and water bath. The resulting solution is extracted with a solvent such as ethylether, ethylacetate, benzene, etc. and the extract is concentrated under reduced pressure, followed by recrystallization or silica gel chromatography.

Process II (Alternative method of producing Compound [VII])

Compound [Ia] can also be produced by the method described in the following Flow Sheet II.

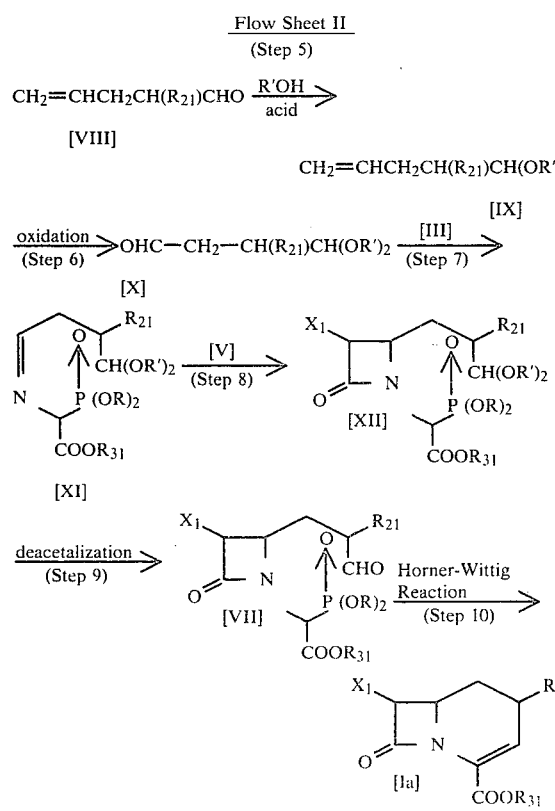

In the compounds of Flow Sheet II, $X_1$, $R_{21}$ and $R_{31}$ have the same significance as defined above and $R'$ represents methyl, ethyl or

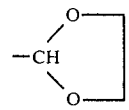

as a group of $-CH(OR')_2$.

Compound [VIII] is a known compound generally synthesized by the Claisen Rearrangement of a substituted allylvinylether represented by $R_{21}-CH=CH-O-CH_2.CH=CH_2$ (Organic Reactions Vol. 22, 1, 1975). Compound [X] can also be obtained by treating Compound [IX] with potassium permanganate to make a diol and oxidative cleavage of the diol with sodium periodate.

Reactions in Flow Sheet II can be carried out under known reaction conditions such as is set forth below.

Step 5

Compound [IX] represented by the general formula [IX]:

$$CH_2=CH.CH_2.CH(R_{21})CH(OR')_2 \qquad [IX]$$

wherein $R'$ and $R_{21}$ have the same significance as defined above, is produced by reacting Compound [VIII] represented by the general formula [VIII]: $CH_2=CHCH_2CH(R_{21})CHO$ wherein $R_{21}$ has the same significance as defined above, with an alcohol represented by $R'OH$, wherein $R'$ has the same significance as defined above, in the presence of an acid and a dehydrating agent.

Suitable acids are hydrochloric acid, sulfuric acid, hydrobromic acid, p-toluenesulfonic acid, borontrifluoride ethyletherate, a carboxylic acid, phosphoric acid, and the like. The acid is used in a catalytic amount. As a dehydrating agent, calcium chloride, a molecular sieve, magnesium sulfate, etc. are appropriate. As the alcohol used in the reaction, methanol, ethanol, ethyleneglycol, etc. are used.

As the solvent, any solvent which does not affect the reaction and preferably benzene, toluene, xylene, and the like are utilized.

The reaction is carried out at room temperature or with heating under reflux for 1 to 24 hours, after which isolation of the desired compound is carried out by known methods.

Step 6

Compound [X] represented by the general formula [X]:

$$OHC-CH_2-CH(R_{21}).CH(OR')_2$$

wherein $R_{21}$ and $R'$ have the same significance as defined above, is produced according to a similar method as in Step 3 in Process 1 from Compound [IX] obtained in Step 5.

Step 7

Compound [IX] represented by the general formula [XI]

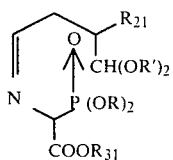

wherein $R_{21}$, R', R and $R_{31}$ have the same significance as defined above, is produced according to a similar method as in Step 1 of Process I from Compound [X] obtained in Step 6 and Compound [III].

Step 8

Compound [XIII] represented by the general formula [XII]

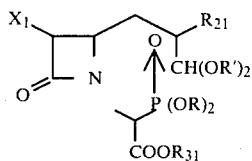

wherein $X_1$, $R_{21}$, R', R, and $R_{31}$ have the same significance as defined above, is produced according to a similar method as in Step 2 of Process I from Compound [XI] obtained in Step 7 and Compound [V].

Step 9

Compound [VII] represented by the general formula [VII]:

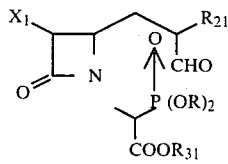

wherein $X_1$, $R_{21}$, R, and $R_{31}$ have the same significance as defined above, is produced by deacetalization of Compound [XII] obtained in Step 8.

Appropriate deacetalization methods include (1) a method wherein Compound [XII] is hydrolyzed with an acid in a solvent such as water or a mixture of water and an organic solvent; and (2) a method wherein Compound [XII] is subjected to an acetal exchange reaction with a carbonyl compound in the presence of a catalytic amount of an acid in a solvent.

In the methods mentioned above, suitable acids are selected from hydrochloric acid, sulfuric acid, p-toluenesulfonic acid, phosphoric acid, acetic acid, boron trifluoride etherate, and the like. As the solvent used in the acetal exchange, hydrocarbons, aromatic hydrocarbons, halogenated hydrocarbons, ethers, esters, etc. are used. The carbonyl compounds may also be used as the solvent; and acetone is preferably used as a carbonyl compound and as the solvent.

The reactions are carried out at room temperature or elevated temperature, for instance the refluxing temperature of the solvent used for a few minutes to several days.

Step 10

The reaction of Step 10 is carried out in a similar manner as in Step 4 of Process I.

Process III

Compound [Ib] represented by the general formula [I] wherein X is an azido group or phthalylimino group, $R_1$ is a lower alkylthio group, an arylthio group, an aralkylthio group or an arylseleno group, $R_2$ is hydrogen atom, $R_3$ is a substituted or unsubstituted alkyl group, an aryl group or an aralkyl group, is produced as is set forth in the following Flow Sheet III.

Flow Sheet III

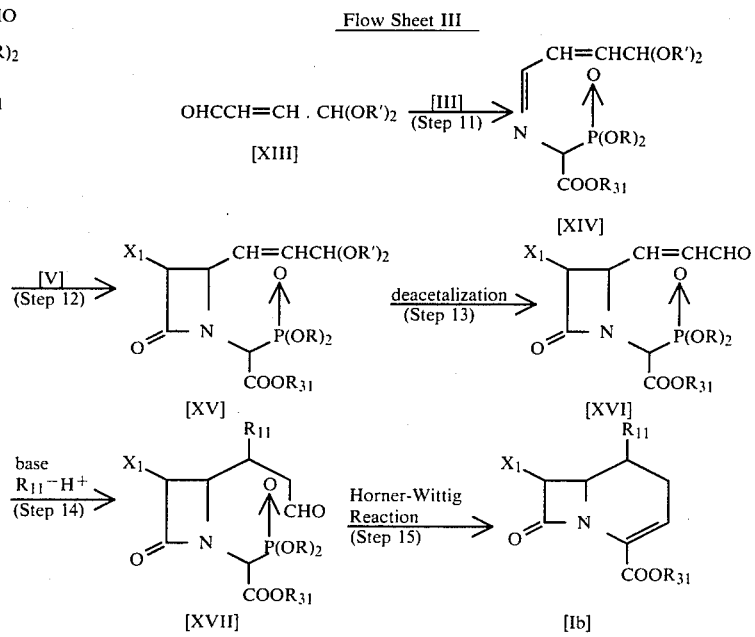

In the compounds of Flow Sheet III, $X_1$, $R_{31}$ and R' have the same significance as defined above, and $R_{11}$ represents a lower alkylthio group, an arylthio group, an aralkylthio group or an arylseleno group.

Compound [XIII] is a known compound which can be synthesized by the method, for example, described in Izvestiia Akademii Nauk USSR, 2189 (1962).

Reactions in Flow Sheet III are carried out under known reaction conditions as is set forth below.

Step 11

Compound [XIV] represented by the general formula [XIV]:

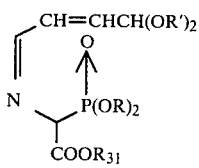

wherein R', R, and $R_{31}$ have the same significance as defined above, is produced according to similar methods as in Step 1 of Process I and Step 7 of Process II, from Compound [XIII] represented by the general formula [XIII]: $OHC.CH=CH.CH(OR')_2$ wherein R' has the same significance as defined above.

Step 12

Compound [XV] represented by the general formula [XV]:

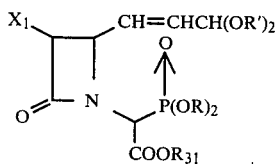

wherein $X_1$, R', R, and $R_{31}$ have the same significance as defined above is produced according to a similar method as Step 2 of Process I and Step 8 of Process II from Compound [XIV] obtained in Step 11 and Compound [V].

Step 13

Compound [XVI] represented by the general formula [XVI]:

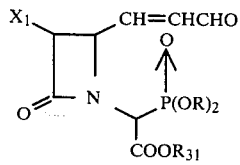

wherein $X_1$, R, and $R_{31}$ have the same significance as defined above, is produced by deacetalization of Compound [XV] obtained in Step 12. The deacetalization can be carried out according to similar methods as in Step 9 of Process II. The acetalization in this step is more readily performed than in Step 9 of Process II. Most preferably, the deacetalization is carried out in the presence of p-toluenesulfonic acid at room temperature in acetone.

Step 14

Compound [XVII] represented by the general formula [XVII]:

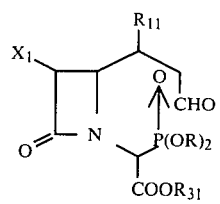

wherein $X_1$, R, $R_{11}$, and $R_{31}$ have the same significance as defined above, is produced by the addition reaction between Compound [XVI] obtained in Step 13 and the compound represented by the general formula $R_{11}H$ wherein $R_{11}$ represents a lower alkylthio, arylthio, aralkylthio or arylseleno group. The addition reaction is carried out in the presence of a base such as sodium hydride, butyllithium, piperidine, and pyrrolidine, in a solvent.

As the solvent, any solvents which do not affect the reaction, and preferably aromatic hydrocarbons such as benzene, toluene, xylene, etc.; alcohols such as methanol, ethanol, or ethers such as dimethyl cellosolve, tetrahydrofuran, are used.

When sodium hydride or butyllithium is used as the base, the reaction is carried out at a temperature of $-70°$ to $-40°$ C., the compound represented by the general formula $R_{11}H$ is used in an amount of 2 to 5 equivalents to Compound [XVI], and the base is used in an amount of 1 to 1.2 equivalents to Compound [XVI].

When an amine such as piperidine or pyrrolidine is used as the base, the reaction is carried out at room temperature or elevated temperature, the compound represented by the general formula $R_{11}H$ is used in an amount of one equivalent or slightly excess to Compound [XVI], and a catalytic amount of base is sufficient. The reaction is carried out for 1 to 3 hours to obtain Compound [XVII].

Step 15

Compound [Ib] represented by the general formula [Ib]:

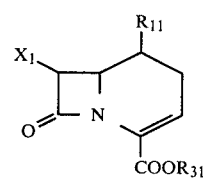

wherein $X_1$, $R_{11}$, and $R_{31}$ have the same significance as defined above, is produced by condensation reaction of Compound [XVII] obtained in Step 14 to form a ring. The ring closure is carried out according to similar methods as in Step 4 of Process I and Step 10 of Process II.

Process IV

Compound [Ic] represented by the general formula [I] wherein X and $R_3$ have the same significance as defined above, $R_1$ is a hydrogen atom, $R_2$ is a halogen atom such as chloro, bromo and iodo, can be produced according to the method illustrated in Flow Sheet IV by using Compound [Ia'] represented by the general formula [Ia] wherein $R_2$ is H as the starting material.

Flow Sheet IV

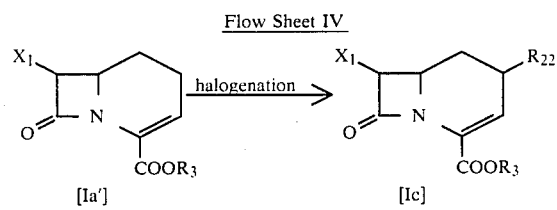

In the compounds of Flow Sheet IV, $R_3$ has the same significance as defined above, $R_{22}$ represents a halogen atom such as chloro, bromo or iodo.

Compound [Ia'], the starting material, is Compound [Ia] represented by the general formula [Ia] wherein $R_{21}$ is H.

The halogenation is generally carried out by using a halogenation reagent employed in the halogenation of an allylic methylene, such as N-halosuccinimide, N-haloacetamide, pyrrolidonehydrotribromide, and the like, preferably using a halogenated hydrocarbon such as dichloromethane, chloroform, carbon tetrachloride as a solvent and preferably at a temperature of room temperature or the refluxing temperature of the solvent. The addition of a reaction initiator such as perbenzoic acid, azobisisobutyronitrile, etc. in the reaction increases the yield.

Process V

Compound [Id] represented by the general formula [Id], i.e. the general formula [I] wherein X and $R_3$ have the same significance as defined above, $R_1$ represents hydrogen atom, $R_2$ represents fluoro, a hydroxyl group, an alkyl group, an acyloxy group, an alkoxy group, an aryloxy group, an aralkyloxy group, an alkylthio group, an arylthio group, an aralkylthio group, a primary, secondary or tertiary amino group, azido group or nitrile group can be produced according to the method illustrated in Flow Sheet V by using Compound [Ic] as the starting material.

Flow Sheet V

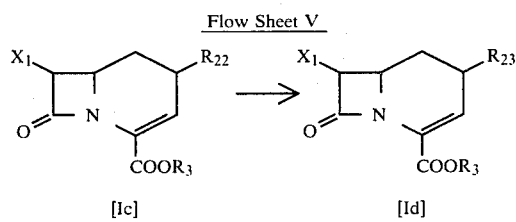

In the compounds of Flow Sheet V, $X_1$, $R_{22}$ and $R_3$ have the same significance as defined above, $R_{23}$ represents fluoro, a hydroxyl group, an alkyl group, an acyloxy group, an alkoxy group, an aryloxy group, an aralkyloxy group, an alkylthio group, an arylthio group, an aralkylthio group, a primary, secondary or tertiary amino group, an azido group or a nitrile group.

In this reaction, Compound [Id] can be prepared by the substitution of the halogen atom in Compound [Ic] for a nucleophilic group $R_{23}$.

Process VI

Compound [Ie] represented by the general formula [I] wherein $R_3$ has the same significance as defined above, X represents an azido or phthalylimino group, $R_2$ represents a hydrogen atom, $R_1$ represents an alkylsulfinyl group, an arylsulfinyl group, an aralkylsulfinyl group or arylseleninyl group, or represented by the general formula [Ie] wherein $X_1$ has the same significance as defined above, $R_{12}$ represents a lower alkyl, aryl or aralkyl group, Y represents a sulfur atom or selenium atom can be produced according to the method illustrated in Flow Sheet VI by using Compound [Ib'] represented by the general formula [I] wherein $X_1$ has the same significance as defined above, $R_2$ represents a hydrogen atom, $R_1$ represents $YR_{12}$ wherein Y and $R_{12}$ have the same significance as defined above or represented by the general formula [Ib] wherein $X_1$ has the same significance as defined above, $R_{31}$ represents $R_3$, $R_{11}$ represents $YR_{12}$ wherein Y and $R_{12}$ have the same significance as defined above as the starting material.

Flow Sheet VI

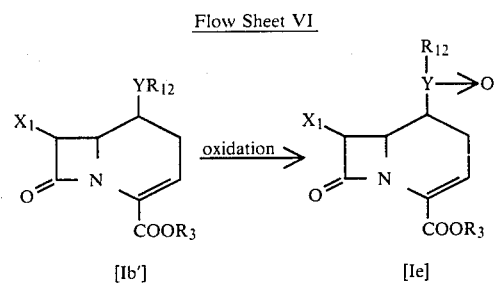

In the Compounds of Flow Sheet VI, $X_1$, $R_3$ and $R_{12}$ have the same significance as defined above.

As the oxidizing agent, an organic peroxide such as periodic acid or salts thereof, hydrogen peroxide, an organic peracid such as methachlorobenzoic acid, or chlorogold acid is suitable.

Process VII

Compound [If] represented by the general formula [I] wherein $R_3$ represents a hydrogen atom can be produced according to the method of Flow Sheet VII by using Compound [I'] represented by the general formula [I] wherein $R_3$ represents $R_{31}$ as the starting material.

Flow Sheet VII

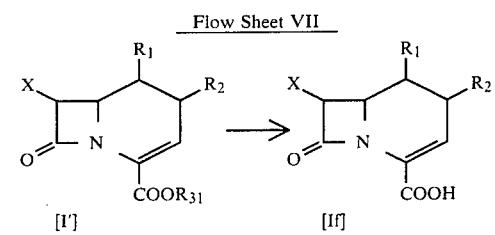

In the compounds of Flow Sheet VII, X, $R_1$, $R_2$ and $R_{31}$ have the same significance as defined above.

The reaction can be carried out by conventional means employed in the field of the synthetic chemistry of penicillins or cephalosporins. In the reaction, Compound [If] can be produced by selecting suitable conditions and reagents to avoid the decomposition of substituents or functional groups of the carbacephem molecule.

Suitable reactions which convert the $-COOR_{31}$ group to a $-COOH$ group include: (1) catalytic reduction; (2) acidolysis; (3) cleavage reaction using a Lewis acid; (4) hydrolysis; (5) reduction other than catalytic reduction using reducing agents; and (6) a method using an esterase; each of which are described below.

(1) Catalytic reduction

In this reaction, the COOR$_{31}$ group is converted to a COOH group in the presence of a catalyst in a hydrogen atmosphere in an inactive solvent. As the solvent, any solvent which does not affect the reaction, and preferably ethanol, water, tetrahydrofuran, dioxane, ethyl acetate and acetic acid, may be used alone or in combination. As the catalyst, palladium-carbon, platinum oxide, palladium-calcium carbonate and Raney nickel are suitable. The reaction is generally carried out at a pressure of 1 to 50 atmospheres and a temperature of 0° to 100° C., preferably at atmospheric pressure and room temperature.

This method is preferably employed when R$_{31}$ is a benzyl group, p-nitrobenzyl group, diphenylmethyl group, p-methoxybenzyl group or the like.

When X is an azido group, the azido group may be reduced to an amino group when R$_{31}$ is converted to H by catalytic reduction. The resulting compound having an amino group is also a desired compound of the present invention.

(2) Acidolysis

In this reaction, the COOR$_{31}$ group is converted to a COOH group with an acid in an inactive solvent. As the acid, hydrogen chloride, p-toluenesulfonic acid, trifluoroacetic acid, etc. are suitable. As the solvent, any solvent which does not affect the reaction, preferably ethyl acetate, benzene, ethanol, acetic acid, dioxane, methylene chloride and chloroform, may be used alone or in combination.

The reaction is generally carried out at a temperature of −15° to 50° C., preferably 0° to 25° C., for 10 minutes to 5 hours, preferably 30 minutes to 3 hours.

This method is preferably used when R$_{31}$ is a t-butyl group, trityl group and so on.

(3) Cleavage reaction using a Lewis acid

In this reaction, the COOR$_{31}$ group is converted to a COOH group by cleavage in the presence of a Lewis acid in an inactive solvent such as any solvent which does not affect the reaction, preferably a mixture of a nitroalkane such as nitromethane and a haloalkane such as methylene chloride. As the Lewis acid, aluminum chloride, boron trifluoride, titanium tetrachloride, tin tetrachloride, and the like are used. The acid is used in an amount of 1.0 to 1.5 molar equivalents to Compound [I']. The reaction is preferably carried out in the presence of an agent which uptakes carbonium cation, such as anisole. The reaction is carried out at a temperature of 0° to 50° C., preferably at room temperature for 1 to 10 hours.

This method is preferably used when R$_{31}$ is a p-nitrobenzyl group and so on.

(4) Hydrolysis

In this reaction, the COOR$_{31}$ group is converted to a COOH group by hydrolysis in the presence of an acid or alkali in an inactive solvent. Suitable acids include p-toluenesulfonic acid, hydrochloric acid, acetic acid, and the like. Any solvent which does not affect the reaction may be used and preferably 2% aqueous methanol, N,N-dimethylformamide, acetic acid-water-tetrahydrofuran are employed. The reaction is generally carried out at a temperature of 0° to 50° C., preferably 15° to 25° C. for 10 minutes to 2 hours.

This method utilizing an acid is preferably used when R$_{31}$ is a t-butyldimethylsilyl group.

As the alkali, calcium carbonate is preferably used in an amount of 1 to 6 molar equivalents to Compound [I']; and any solvent which does not affect the reaction and preferably tetrahydrofuran-water, dioxane-water, acetone-water, are used. The reaction is generally carried out at a temperature of 0° to 30° C. for 30 minutes to 24 hours.

This method utilizing an alkali is preferably employed when R$_{31}$ is a methyl group, ethyl group and so on.

(5) Reduction using reducing agents (other than catalytic reduction)

In this reaction, the COOR$_{31}$ group is converted to a COOH by reduction in an inactive solvent, for example using a zinc-acid method. For this reaction a solvent such as acetone, water, dioxane, tetrahydrofuran, ethanol, acetonitrile, N,N-dimethylformamide and acetic acid may be used alone or in combination. As the acid, hydrochloric acid and acetic acid are suitable. The reaction is carried out at a temperature of 0° to 100° C., preferably 0° to 40° C. for 1 to 10 hours. The amount of zinc used for the reaction is usually 1 to 10 molar equivalents.

This method is preferably employed when R$_{31}$ is 2,2,2-trichloroethyl and so on.

Process VIII

Compound [Ih] represented by the general formula [I] wherein X represents NH$_2$ can be produced according to the method of Flow Sheet VIII by using Compound [Ig] represented by the general formula [I] wherein X represents N$_3$ as the starting material.

Flow Sheet VIII

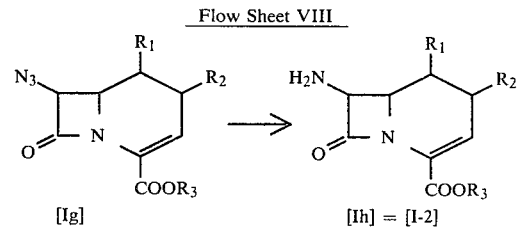

[Ig]  [Ih] = [I-2]

The reaction is carried out using conventional methods employed in the field of synthetic chemistry of penicillins or cephalosporins. In the reaction, Compound [Ih] can be produced by selecting suitable conditions and reagents to avoid the decomposition of substituents or functional groups of the carbacephem molecule.

Suitable reduction methods include: (1) catalytic reduction; (2) reduction using hydrogen sulfide and tertamine; (3) reduction using sodium borohydride; (4) reduction using zinc-acid; and (5) reduction using chromium (II) chloride, as are set forth below.

(1) Catalytic reduction

Compound [Ig] is subjected to catalytic reduction in a stream of hydrogen gas in the presence of a catalyst in an inactive solvent to obtain Compound [I-2]. Any solvent which does not affect the reaction may be used. Preferably ethanol, water, tetrahydrofuran, dioxane, ethyl acetate, acetic acid, or a mixture thereof is employed. As the catalyst, palladium-carbon, platinum oxide, palladium-calcium carbonate and Raney nickel are appropriate.

The reaction is generally carried out at a temperature of 0° to 100° C., preferably at room temperature, and at a pressure of 1 to 50 atmospheres, preferably at atmospheric pressure.

In this reaction, when a compound represented by the general formula [Ig] wherein R$_3$ is a substituted arylmethyl group such as benzyl group, paramethoxybenzyl group, paranitrobenzyl group, benzhydryl group, trityl group, etc. is used as the starting material, a compound represented by the general formula [Ih] wherein $R_3$ is hydrogen may also be obtained.

(2) Reduction using hydrogen sulfide-tert-amine

Compound [Ig] is reduced with hydrogen sulfide and tert-amine in the presence of a base in an inactive solvent to obtain Compound [I-2]. As the solvent, methylene chloride, chloroform, and the like are used alone or in combination. As the base, triethylamine, pyridine, and the like are appropriate.

The reaction is carried out at a temperature of 0° to 50° C., preferably at room temperature.

(3) Reduction using sodium borohydride

Compound [Ig] is reduced with sodium borohydride in an inactive solvent to obtain Compound [I-2]. As the solvent, methanol, ethanol, dioxane, tetrahydrofuran are used alone or in combination. Sodium borohydride is used in an amount of one equivalent or excess to Compound [Ig].

The reaction is carried out at a temperature of 0° to 100° C., preferably 10° to 50° C.

(4) Reduction using zinc-acid

Compound [Ig] is reduced with zinc-acid in an inactive solvent to obtain Compound [I-2]. As the solvent, acetone, water, dioxane, tetrahydrofuran, ethanol, acetic acid are used alone or in combination. As the acid, hydrochloric acid or acetic acid are suitable. Zinc and the acid are used in an amount of one equivalent or excess to Compound [Ig].

The reaction is carried out at a temperature of 0° to 100° C., usually room temperature to 60° C.

(5) Reduction using chromium (II) chloride

Compound [Ig] is reduced with chromium (II) chloride in the presence of an acid in an inactive solvent. The acid, solvents, and reaction conditions are the same as in method (4) above.

The desired compounds of the present invention, represented by the general formula [I] and produced according to Processes I to VIII, are useful as intermediates for synthesizing carbacephalosporins having skeletons analogous to cephalosporins. The azido group and phthalylimino group of Compound [I] are converted to an amino group to prepare Compound [Ih] represented by the general formula [I] wherein X represents $NH_2$. Compound [Ih] is further converted to a compound represented by the general formula

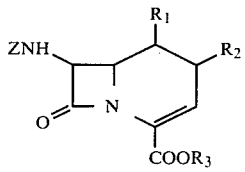

wherein Z is an acyl group and $R_1$, $R_2$ and $R_3$ have the same significance defined above. Conventional acyl groups employed in the field of the synthetic chemistry of penicillins and cephalosporins are introduced to the amino group to obtain cephalosporin analogs having strong antibacterial activity.

As the salts of Compound [I] (cephalosporin analogs), the salts of inorganic or organic acids such as the hydrochloride, sulfate, phosphate, formate, and malate of Compound [Ih] represented by the general formula [I] wherein X represents $NH_2$ and the salts of inorganic or organic bases such as the sodium salts, potassium salt, calcium salt, organic amine salt, etc. of the carboxylic acid of Compound [If] represented by the general formula [I] wherein $R_3$ represents H are appropriate.

Certain specific embodiments of the invention are illustrated by the following representative examples.

EXAMPLE 1

Preparation of ($\pm$)-cis-2-t-butyloxycarbonyl-7-azido-1-azabicyclo[4,2,0]oct-2-en-8-one, i.e. the cis-compound represented by the general formula [I] wherein X is $N_3$, $R_1$ and $R_2$ are H and $R_3$ is $^tBu$, represented by the general formula [Ia] wherein $X_1$ is $N_3$, $R_{21}$ is H and $R_{31}$ is $^tBu$ and represented by the following formula:

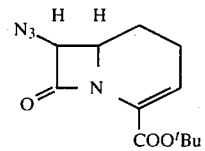

The compound is produced according to the following Processes 1 and 2; and, as used hereinafter, cis and trans mean the stereoisomers at the 3- or 4-position of the 2-azetidinone ring or at the 6- or 7-position of the 1-azabicyclo[4,2,0]octane ring.

(1) Preparation of 2-[4-(3-butenyl)-3-azido-2-oxoazetidin-1-yl]-2-diethylphosphonoacetate-t-butylester, i.e., the compound represented by the general formula [VI] wherein $X_1$ is $N_3$, $R_{21}$ is H and $R_{31}$ is $^tBu$.

In this Example, 447 mg. (1.78 m mole) of t-butyl-$\alpha$-aminodiethylphosphonoacetate, the compound represented by the general formula [III] wherein $R_{31}$ is $^tBu$, R is ethyl and being characterized as: an oily product; IR (neat) $\nu_{max}^{cm-1}$ 3400, 1735–1745, 1020–1060; NMR (CDCl$_3$)$\delta$(ppm), 4.20 (d-q, 4H), 3.83 (d, 1H, J=20 Hz), 1.76 (br, 2H), 1.50 (s, 9H), 1.35 (t, 6H); Mass (m/e): 268(M+) is dissolved in 25 ml of anhydrous ether and 164 mg. (1.96 mmole) of 4-pentene-1-al is added to the solution. The solution is stirred at room temperature for one hour and then 200 mg. of Molecular Sieve (4A) (product of Wako Junyaku Co., Ltd.) and 150 mg. of anhydrous magnesium sulfate are added to the solution and the mixture is then stirred for an additional hour. The same molecular sieve is also used hereinafter.

The reaction mixture is then subjected to filtration under reduced pressure and the filtrate is concentrated under reduced pressure to obtain a pale yellow oily product. Anhydrous benzene is added to the product and the mixture is concentrated under reduced pressure to obtain a pale yellow oily product. The presence of Shiff's base in the product is confirmed by nuclear magnetic resonance spectrum. The product is then dissolved in 12.5 ml of cyclohexane and 12.5 ml of anhydrous benzene, and 0.369 ml (2.66 mmole) of triethylamine and 200 mg. of Molecular Sieve 4A are added to the solution. Azidoacetylchloride [319 mg. (2.66 mmole)] dissolved in 12.5 ml of cyclohexane is added dropwise to the mixture with stirring at room temperature in about 1.5 hours. The reaction mixture is then stirred for an additional 30 minutes and diluted with 10 ml of benzene. The reaction solution is washed with 5% diluted hydrochloric acid, saturated sodium bicarbonate, deionized water and saturated sodium chloride solution, dried with anhydrous sodium sulfate and concentrated under reduced pressure to obtain a brown oily product which is identified as a crude product of the desired compound represented by the general formula [VI] wherein $X_1$ is $N_3$, $R_{21}$ is H and $R_{31}$ is $^tBu$.

The oily product is charged on a column packed with 45 g of Wako-gel C-200 (silica gel product of Wako Junyaku Co., Ltd.), the same silica gel is used hereinafter. Elution is carried out with a mixture of n-hexane and ethyl acetate (1:2, by volume, which is also used hereinafter) to obtain two types of isomers. The properties of the isomers are set forth below and they are identified as the isomers at the 3- and 4-positions, i.e. 345 mg. of cis-isomer and 58 mg. of trans-isomer. Total yield is 54.2%.

Cis-isomer

IR (CHCl$_3$) $\nu_{max}{}^{cm-1}$: 2120, 1775, 1770(sh), 1750, 1740(sh), 1645.

NMR (CDCl$_3$)δ(ppm): 6.13–6.33(1H, m), 4.93–5.17(2H, m), 4.50–4.93(2H, m), 3.80–4.40(5H, m), 1.93–2.17 (4H, m), 1.50(9H, s), 1.33(6H, t).

Trans-isomer

IR (CHCl$_3$) $\nu_{max}{}^{cm-1}$: 2120, 1780, 1755, 1750(sh), 1650.

NMR (CDCl$_3$)δ(ppm): 5.43–6.20(1H, m), 4.80–5.30 (2H, m), 3.75–4.75(7H, m), 2.0–2.50(4H, m), 1.50(9H, d), 1.17(6H, m).

(2) Preparation of (±)-cis-2-t-butyloxycarbonyl-7-azido-1-azabicyclo[4,2,0]oct-2-en-8one, i.e. the cis-isomer of the compound represented by the general formula [I] wherein X is N$_3$, R$_1$ and R$_2$ are H and R$_3$ is $^t$Bu.

In this example, 298 mg. (0.716 mmole) of cis-2-[4-(3-butenyl)-3-azido-2-oxoazetidin-1-yl]-2-diethylphosphonoacetate-t-butylester obtained in Example 1-1 is dissolved in 8.5 ml of dioxane and 2.5 ml of deionized water, and 30 mg. of osmium tetroxide is added thereto. The solution is stirred for 30 minutes. Powdered sodium periodate [496 mg. (2.32 mmole)] is added to the black reaction mixture in 20 minutes. After stirring for 1.5 hours, the reaction solution is extracted three times with 50 ml of ether and the ether extracts are combined and washed with saturated sodium chloride solution. The resulting solution is dried with anhydrous sodium sulfate and concentrated under reduced pressure to obtain a dark-brown oily product.

The product is then charged on a column packed with 5 g of silica gel and elution is carried out with a solvent of benzene and ethyl acetate (1:2). Fractions which are positive to 2,4-dinitrophenylhydrazine reaction are collected and concentrated to obtain 235 mg. of an oily product which is the cis-isomer of the aldehyde compound represented by the general formula [VII] wherein X$_1$ is N$_3$, R$_{21}$ is H and R$_{31}$ is $^t$Bu. The oily product is then dissolved in 15 ml of anhydrous acetonitrile. Sodium hydride [50%, 27.1 mg. (0.563 mmole)] is added to the solution in a stream of nitrogen with stirring at room temperature. After stirring for 20 minutes, the reaction mixture is poured into 20 ml of 2% aqueous acetic acid and the solution is extracted with 50 ml of ether four times. The ether extracts are combined and washed with saturated sodium chloride solution. The resulting solution is then dried with anhydrous sodium sulfate and concentrated under reduced pressure to obtain 180 mg. of an oily product which is identified as a crude product of the desired cis-compound represented by the general formula [I] wherein X is N$_3$, R$_1$ and R$_2$ are H and R$_3$ is $^t$Bu.

The oily product is charged on a column packed with 5 g of silica gel and elution is carried out with a solvent of n-hexane and ethylacetate (3.5:1, by volume) to obtain 91 mg. of the desired compound as white crystals. Yield 51%. Properties of the compound are as follows.

Melting point: 64.5°–65.5° C.

IR (CHCl$_3$) $\nu_{max}{}^{cm-1}$: 2130, 1790, 1730, 1640.

NMR (CDCl$_3$)δ(ppm): 6.30(1H, t, J=4 Hz), 4.93(1H, d, J=5 Hz), 3.80(1H, q), 1.6–2.6(4H, m), 1.52 (9H, s).

EXAMPLE 2

Preparation of (±)-trans-2-t-butyloxycarbonyl-7-azido-1-azabicyclo[4,2,0]oct-2-en-8-one, i.e. the trans-compound represented by the general formula [I] wherein X is N$_3$, R$_1$ and R$_2$ are H and R$_3$ is $^t$Bu, represented by the general formula [Ia] wherein X$_1$ is N$_3$, R$_{21}$ is H and R$_{31}$ is $^t$Bu and represented by the following formula:

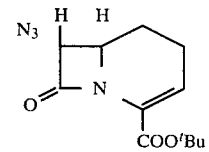

In this Example, 767 mg. (1.84 mmole) of trans-2-[4-(3-butenyl)-3-azido-2-oxoazetidin-1-yl]-2-diethylphosphonoacetate-t-butylester obtained as in Example I-1 is dissolved in 22 ml of dioxane and 6.5 ml of deionized water, and 100 mg. of osmium tetroxide is added thereto. The mixture is stirred for 30 minutes. Powdered sodium periodate [1.5 g (7.04 mmole)] is added to the black reaction mixture in 30 minutes. After stirring for one hour, the reaction mixture is extracted three times with 150 ml of ether. The ether extracts are combined and dried with anhydrous sodium sulfate. The resulting solution is then concentrated under reduced pressure to obtain an oily product.

The oily product is then charged on a column packed with 20 g of silica gel and elution is carried out with a solvent of benzene and ethyl acetate (1:2). The fractions which are positive to 2,4-dinitrophenyl-hydrazine reaction are combined from which 561 mg. of an oily product is obtained. This product is the trans-compound of the aldehyde compound represented by the general formula [VII] wherein X$_1$ is N$_3$ and R$_{31}$ is $^t$Bu. The product is dissolved in 6 ml of anhydrous acetonitrile and 61.4 mg. (2.56 mmole) of 50% sodium hydride is added thereto. The mixture is heated to a temperature of 50° C. and allowed to react for ten minutes. Then, the reaction mixture is poured into 6 ml of 2% aqueous acetic acid and extracted four times with 50 ml of ether. The ether extracts are combined and dried with anhydrous sodium sulfate. The resulting solution is then concentrated under reduced pressure to obtain an oily product which is then charged on a column packed with 20 g of silica gel and elution is carried out with a solvent of n-hexane and ethyl acetate (3.5:1) whereby 218 mg. of the desired compound is obtained as white crystals. The compound is identified as trans-isomer of the desired compound represented by the general formula [I] wherein X is N$_3$, R$_1$ and R$_2$ are H and R$_3$ is $^t$Bu, the properties of which are as follows.

Melting point: 80.5°–81.5° C.

IR (CHCl$_3$) $\nu_{max}{}^{cm-1}$: 2110, 1780, 1720, 1635.

NMR (CDCl$_3$)δ(ppm): 6.27(1H, t), 4.28(1H, d, J=2 Hz), 3.53(1H, q), 2.0–2.6(4H, m), 1.63(9H, s).

EXAMPLE 3

Preparation of (±)-cis-2-carboxy-7-azido-1-azabicyclo[4,2,0]oct-2-en-8-one, i.e., the cis-compound represented by the general formula [I] wherein X is N$_3$ and R$_1$, R$_2$ and R$_3$ are H, represented by the general formula

[Ia] wherein $X_1$ is $N_3$ and $R_{21}$ and $R_{31}$ are H and represented by the following formula:

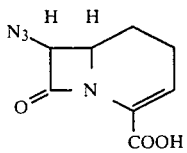

In this Example, 55 mg. (0.224 mmole) of (±)-cis-2-t-butyloxycarbonyl-7-azido-1-azabicyclo[4,2,0]oct-2-en-8-one obtained in Example 1 is dissolved in 2 ml of trifluoroacetic acid and the solution is allowed to stand at room temperature for 10 minutes. The solution is concentrated under reduced pressure. Benzene is added to the concentrate and the resulting solution is concentrated under reduced pressure to obtain 51 mg. of a yellow semi-solid having the following properties from which it is identified as the desired carboxylic acid. Yield 100%.

IR (CHCl$_3$) $\nu_{max}^{cm-1}$: 2120, 1170(sh), 1760, 1715, 1635.

NMR (CD$_3$OD)$\delta$(ppm): 6.48(1H, t, J=4 Hz), 5.10(1H, d, J=5 Hz), 3.83(1H, q), 1.1–2.5(4H, m).

EXAMPLE 4

Preparation of (±)-cis-2-t-butyloxycarbonyl-4-bromo-7-azido-1-azabicyclo[4,2,0]oct-2-en-8-one, i.e., the cis-compound represented by the general formula [I] wherein X is $N_3$, $R_1$ is H, $R_2$ is Br and $R_3$ is $^tBu$, represented by the general formula [Ic] wherein $X_1$ is $N_3$, $R_{22}$ is Br and $R_3$ is $^tBu$ in Process V, and represented by the following formula:

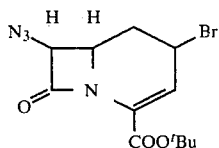

In this Example, 50 mg. (0.203 mmole) of (±)-cis-2-t-butyloxycarbonyl-7-azido-1-azabicyclo[4,2,0]oct-2-en-8-one obtained in Example 1 is dissolved in 2 ml of anhydrous chloroform, and 36.0 mg. (0.202 mmole) of N-bromosuccinimide and a catalytic amount of azobisisobutyronitrile are added thereto. The mixture is heated under reflux with stirring for 30 minutes and is then diluted with 5 ml of chloroform. The diluted solution is washed with 3 ml of water and 3 ml of saturated sodium chloride solution, and then dried with anhydrous sodium sulfate. The resulting solution is concentrated under reduced pressure to obtain 53 mg. of an oily product.

The oily product is charged on a column packed with 4.0 g of silica gel and elution is carried out with a solvent of n-hexane and ethyl acetate (3.5:1) whereby 23 mg. of an oily product is obtained. The product is identified as the desired cis-compound represented by the general formula [Ic] wherein $X_1$ is $N_3$, $R_{22}$ is Br and $R_3$ is $^tBu$ from the following properties. Yield 33%.

IR (CHCl$_3$) $\nu_{max}^{cm-1}$: 2120, 1790, 1730, 1620.

NMR (CDCl$_3$)$\delta$(ppm): 6.33(1H, d, J=6 Hz), 5.07(1H, d, J=5 Hz), 4.93(1H, m), 4.50–3.90(1H, m), 2.50–1.72 (2H, m), 1.52(9H, s).

EXAMPLE 5

Preparation of (±)-trans-2-t-butyloxycarbonyl-4-bromo-7-azido-1-azabicyclo[4,2,0]oct-2-en-8-one, i.e., the trans-compound represented by the general formula [I] wherein X is $N_3$, $R_1$ is H, $R_2$ is Br and $R_3$ is $^tBu$, represented by the general formula [Ic] wherein $X_1$ is $N_3$, $R_{22}$ is Br and $R_3$ is $^tBu$ in Process IV and represented by the following formula:

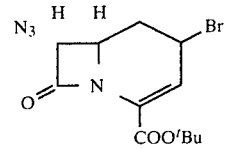

In this Example, 100 mg. (0.407 mmole) of (±)-trans-2-t-butyloxycarbonyl-7-azido-1-azabicyclo[4,2,0]oct-2-en-8-one obtained in Example 2 is dissolved in 5 ml of anhydrous carbon tetrachloride and 72.4 mg. of N-bromosuccinimide is added thereto. The mixture is heated under reflux with stirring for 30 minutes. Thereafter, 10 ml of methylenechloride is added to the reaction mixture and the resulting mixture is washed with 5 ml of deionized water and 5 ml of saturated sodium chloride solution. The resulting solution is dried with anhydrous sodium sulfate and concentrated under reduced pressure to obtain 102 mg. of an oily product.

The oily product is charged on a column packed with 5 g of silica gel and elution is carried out with a solvent of n-hexane and ethyl acetate (3.5:1) whereby 24 mg. of an oily product is obtained. The product is identified as the desired trans-compound represented by the general formula [Ic] wherein X is $N_3$, $R_{22}$ is Br and $R_3$ is $^tBu$ from the following properties. Yield 18.1%.

IR (CHCl$_3$) $\nu_{max}^{cm-1}$: 2130, 1790, 1730, 1620

NMR (CDCl$_3$)$\delta$(ppm): 6.23(1H, d, J=6 Hz), 5.93(1H, m), 4.37(1H, d), 4.00(1H, m), 2.93–1.93(2H, m), 1.50(9H, s).

EXAMPLE 6

Preparation of (±)-cis-2-t-butyloxycarbonyl-4α-acetoxy-7β-azido-1-azabicyclo[4,2,0]oct-2-en-8-one, i.e., the cis-compound represented by the general formula [I] wherein X is $N_3$, $R_1$ is H, $R_2$ is OCOCH$_3$ and $R_3$ is $^tBu$, represented by the general formula [Id] wherein $X_1$ is $N_3$, $R_{23}$ is OCOCH$_3$, and $R_3$ is $^tBu$ and represented by the following formula:

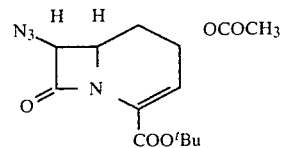

In this Example, 75 mg. (0.219 mmole) of (±)-cis-2-t-butyloxycarbonyl-4-bromo-7-azido-1-azabicyclo[4,2,0]oct-2-en-8-one which is the cis-compound represented by the general formula [Ic] wherein $X_1$ is $N_3$, $R_{22}$ is Br and $R_3$ is $^tBu$ obtained as in Example 4, is dissolved in 2 ml of acetic acid. While protecting the reaction system from light, 39.4 mg. (0.241 mmole) of silver acetate is added to the solution and the mixture is stirred for 2 hours and 20 minutes. The reaction mixture is then subjected to filtration and concentrated under reduced pressure to obtain a crude acetoxy product of the desired compound.

The product is charged on a column packed with 3.5 g of silica gel and elution is carried out with a solvent of n-hexane and ethyl acetate (3.5:1) to obtain 51 mg. of an oily product. The product is identified as the desired cis-compound represented by the general formula [Id] wherein $X_1$ is $N_3$, $R_{23}$ is $OCOCH_3$ and $R_3$ is $^tBu$ from the following properties. Yield 72.1%.

IR $(CHCl_3)$ $\nu_{max}cm^{-1}$: 2130, 1790, 1750, 1730(sh), 1635.

NMR $(CDCl_3)\delta$(ppm): 6.21(1H, d, J=5 Hz), 5.42(1H, m), 5.01(1H, d, J=5 Hz), 3.95(1H, m), 2.02(3H, s), 2.6–1.7(2H, m), 1.53(9H, s).

EXAMPLE 7

Preparation of (±)-cis-2-t-butyloxycarbonyl-4-methyl-7-azido-1-azabicyclo[4,2,0]oct-2-en-8-one, i.e., the cis-compound represented by the general formula [I] wherein X is $N_3$, $R_1$ is H, $R_2$ is $CH_3$ and $R_3$ is $^tBu$, represented by the general formula [Ia] wherein $X_1$ is $N_3$, $R_{21}$ is $CH_3$ and $R_{31}$ is $^tBu$ and represented by the following formula:

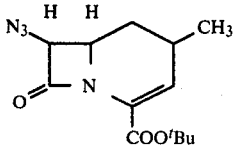

This compound is produced by the following processes (1) and (2).

(1) Preparation of 2-[4-(2-methyl-3-butenyl)-3-azido-2-oxoazetidin-1-yl]-2-diethylphosphonoacetate tert-butylester, the compound represented by the general formula [VI] wherein $X_1$ is $N_3$, $R_{21}$ is $CH_3$, and $R_{31}$ is $^tBu$.

In this example, 2.13 g (8 mmole) of t-butyl-α-amino-diethylphosphonoacetate, the compound represented by the general formula [III] wherein $R_{31}$ is $^tBu$, is dissolved in 80 ml of anhydrous ether and 902 mg. (9.2 mmole) of 3-methyl-4-pentenal is added with stirring. The mixture is stirred at room temperature for one hour and 900 mg. of Molecular Sieve 4A and 700 mg. of magnesium sulfate are then added thereto. After stirring for an additional 1.5 hours, the reaction mixture is subjected to filtration under reduced pressure. The resulting filtrate is concentrated to obtain a pale yellow oily product. Anhydrous benzene (30 ml) is added to the product and the resulting solution is again concentrated to obtain 2.82 g of an oily product. The presence of a Shiff's base in the product is confirmed by NMR spectrum.

The oily product is then dissolved in 56 ml of dried cyclohexane and 56 ml of anhydrous benzene and 900 mg. of Molecular Sieve 4A and 1.67 ml (12 mmole) of triethylamine are added. To this mixture, 1.43 g (12 mmol) of azidoacetylchloride dissolved in 56 ml of dried cyclohexane is added dropwise in 1.5 hours at room temperature with stirring. The mixture is then stirred for an additional 30 minutes and 30 ml of benzene is added thereto. The mixture is transferred into a separatory funnel and washed with 30 ml each of 10% citric acid, saturated sodium chloride solution, saturated sodium bicarbonate, and saturated sodium chloride solution in that order. The resulting solution is dried with anhydrous sodium sulfate and concentrated under reduced pressure to obtain 2.8 g of an oily product. The presence of a mixture of two major isomers in the product is ascertained by thin layer chromatography [silica gel, n-hexane-ethyl acetate (1:1)].

The product is then charged on a column packed with 300 g of silica gel and elution is carried out with a mixed solvent of n-hexane and ethyl acetate (1:1) to obtain 380 mg. (yield 11.0%) of the less polar isomer of the desired compound represented by the general formula [VI] wherein X is $N_3$, $R_{21}$ is $CH_3$ and $R_{31}$ is $^tBu$, 570 mg. (yield 16.7%) of the more polar isomer of the desired compound, and 201 mg. (yield 5.8%) of a mixture of the two isomers.

The properties of each isomer are as follows. From the data, the more polar isomer is identified as the cis-isomer of the desired compound.

The less polar isomer
IR $(CHCl_3)$ $\nu_{max}cm^{-1}$: 2110, 1770, 1745.
NMR $(CDCl_3)\delta$(ppm): 5.40–6.10(1H, m), 5.27–4.90(2.5H, m), 4.68(0.5H, d), 4.23(6H, m), 2.60–1.77(3H, m), 1.53(9H, s), 1.37(6H, t, J=7.0 Hz), 1.10(3H, d, J=6.0 Hz).

The more polar isomer (cis-compound)
IR $(CHCl_3)$ $\nu_{max}cm^{-1}$: 2110, 1765, 1745.
NMR $(CDCl_3)\delta$(ppm): 5.45–6.13(1H, m), 4.83–5.20(2.5H, m), 4.67(0.5H, d), 3.97–4.45(6H, m), 1.77–2.55(3H, m), 1.50(9H, s), 1.33(6H, t), 1.08(3H, d).

(2) Preparation of (±)-cis-2-t-butyloxycarbonyl-4-methyl-7-azido-1-azabicyclo[4, 2, 0]oct-2-en-8-one, the cis-compound represented by the general formula [I] wherein X is $N_3$, $R_1$ is H, $R_2$ is $CH_3$ and $R_3$ is $^tBu$, represented by the general formula [Ia] wherein $X_1$ is $N_3$, $R_{21}$ is $CH_3$ and $R_{31}$ is $^tBu$, and represented by the following formula:

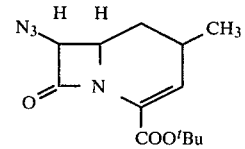

In this example, 240 mg. (0.56 mmole) of the tertbutyl ester of (±)-cis-2-[4-(2-methyl-3-butenyl)-3-azido-2-oxoazetidin-1-yl]-2-diethylphosphonoacetate obtained in Example 7-1, is dissolved in 6.6 ml of dioxane and 2 ml of deionized water. Osmium tetroxide (20 mg.) is added and the mixture is stirred for 10 minutes. Then 390 mg. of powdered sodium periodate (1.82 mmole) is added in small portions to the black reaction solution in 30 minutes.

After stirring for 40 minutes, the reaction solution is subjected to extraction three times with 30 ml of ether and the extracts are combined. The combined extracts are washed with saturated sodium chloride solution, dried with anhydrous sodium chloride, and concentrated to obtain 230 mg. of an oily product. The oily product is charged on a column packed with 6 g of silica gel and elution is carried out with a solvent of benzene and ethyl acetate (1:2). Fractions which are positive to 2,4-dinitrophenylhydrazine reaction are combined and concentrated to obtain 185 mg. of an oily product which is the cis-compound of the aldehyde compound represented by the general formula [VII] wherein $X_1$ is $N_3$, $R_{21}$ is $CH_3$ and $R_{31}$ is $^tBu$. The product is immediately dissolved in 8 ml of anhydrous acetonitrile and 21.6 mg. (0.45 mmole) of 50% sodium hydride is added to the solution in a stream of nitrogen with stirring at room temperature. After stirring for 30 minutes, the reaction solution is poured into 15 ml of 2% aqueous acetic acid and the mixed solution is subjected to extraction twice with 20 ml of ether. The ether layers are washed with saturated sodium chloride solution, dried with anhydrous sodium chloride, and concentrated under reduced pressure to obtain an oily product which is identified as a crude product of the desired cis-compound represented by the general formula [I] wherein X is $N_3$, $R_1$ is H, $R_2$ is $CH_3$ and $R_3$ is $^tBu$.

The oily product is then charged on a column packed with 20 g of silica gel and elution is carried out with a solvent of n-hexane and ethyl acetate (3.5:1, by volume) whereby 70 mg. of the desired compound is obtained as a colorless oily product which crystallizes on standing. Properties of the product are as follows. Yield 48.1%.

IR (KBr) $\nu_{max}^{cm-1}$: 2110, 1784, 1715, 1623.

NMR (CDCl$_3$)δ(ppm): 6.30(4/5H, d, J=5.1 Hz), 6.10(1/5H, d, J=2.7 Hz), 4.98(4/5H, d, J=5.0 Hz), 4.89(1/5H, d, J=5.0 Hz), 3.60-3.90(1H, m), 2.65(1H, m), 1.70-1.80(2H, m), 1.51(9H, s) 1.20(3/5H, d, J=8.0 Hz), 1.13(12/5H, d, J=8.0 Hz).

The thus obtained crystals are identified as a mixture of the 4α-methyl isomer and 4β-methyl isomer in a ratio of about 4:1 by the above NMR data.

EXAMPLE 8

Preparation of (±)-cis-2-t-butyloxycarbonyl-5-phenylthio-7-azido-1-azabicyclo [4, 2, 0] oct-2-en-8-one, i.e., the cis compound represented by the general formula [I] wherein X is $N_3$, $R_1$ is $SC_6H_5$, $R_2$ is H, and $R_3$ is $^tBu$, represented by the general formula [Ib] wherein $X_1$ is $N_3$, $R_{11}$ is $SC_6H_5$ and $R_{31}$ is $^tBu$, and represented by the following formula:

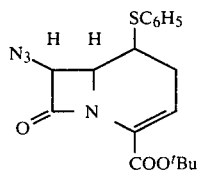

This compound is produced by the following processes (1)-(4).

(1) Preparation of compound [XIV]', the Shiff's base represented by the general formula [XIV] wherein R' is $CH_3$ and $R_{31}$ is $^tBu$.

In this Example, 1.08 g (4 mmole) of t-butyl-α-aminodiethylphosphonoacetate, the compound represented by the general formula [III] wherein $R_{31}$ is $^tBu$, is dissolved in 100 ml of anhydrous methylene chloride and 580 mg. (4.4 mmole) of 4,4-dimethoxy-trans-2-butenal represented by the general formula [XIII] wherein R' is $CH_3$ dissolved in 20 ml of anhydrous methylene chloride is added thereto. The mixture is stirred at room temperature for one hour. Then 600 mg. of anhydrous magnesium sulfate is added to the mixture and the resulting solution is stirred for an additional hour. The reaction solution is then subjected to filtration under reduced pressure and the methylene chloride is evaporated under reduced pressure to obtain 1.63 g of an oily product. Yield 100%.

The product is identified as the Shiff's base of the desired compound represented by the general formula [XIV] wherein R' is $CH_3$ and $R_{31}$ is $^tBu$ from the following properties.

NMR (CDCl$_3$)δ(ppm): 8.00(1H, d-d), 6.67(1H, d-d), 4.93(1H, d), 3.97-4.33(4H, m), 3.33(6H, s), 1.50 (9H, s), 1.33(6H, t).

Mass (m/e): 380 (M+1).

(2) Preparation of Compound [XV]', the acetal compound represented by the general formula [XV] wherein $X_1$ is $N_3$, R' is $CH_3$ and $R_{31}$ is $^tBu$, and Compound [XVI]', the aldehyde compound represented by the general formula [XVI] wherein $X_1$ is $N_3$ and $R_{31}$ is $^tBu$.

In this Example, 1.6 g (4.2 mmole) of the Shiff's base (Compound [XIV]', obtained in Example 8-1) is dissolved in 30 ml of anhydrous benzene and 30 ml of anhydrous cyclohexane and 0.84 ml (7 mmole) of anhydrous triethylamine is added. To the mixture, 580 mg. (4.8 mmole) of azidoacetylchloride dissolved in 40 ml of cyclohexane is slowly added in drops at room temperature in about 1.5 hours. The mixture is then stirred at room temperature for an additional hour. Benzene is then added to the reaction solution and the mixture is washed with saturated sodium bicarbonate and saturated sodium chloride solution. The resulting solution is dried with anhydrous magnesium sulfate and concentrated under reduced pressure to obtain 1.88 g of a crude product.

The product is charged on a column packed with 90 g of silica gel and elution is carried out with a solvent of n-hexane and ethyl acetate (1:2) whereby 550 mg. (28.2%) of Compound [XV]' and 220 mg (11.3%) of Compound [XVI]' are obtained.

Properties of the thus obtained acetal and aldehyde compounds are as follows. The acetal compound:

NMR (CDCl$_3$)δ(ppm): 5.83–6.07(2H, m), 4.50-5.00(3H, m), 4.23(4H, g), 3.33(6H, s), 1.50(9H, s), 1.37(6H, t).

IR (CHCl$_3$) $\nu_{max}^{cm-1}$: 2120, 1780, 1745.

The aldehyde compound:

IR (CHCl$_3$) $\nu_{max}^{cm-1}$: 2120, 1785, 1750, 1700.

NMR (CDCl$_3$)δ(ppm): 9.62(1H, d), 7.00(1H, d-d, J=8 Hz, 15 Hz), 6.26(1H, d-d, J=7 Hz, 15 Hz), 4.84(1H, d, J=24 Hz), 4.80-5.02(2H, m), 4.16(4H, m), 1.46(9H, s), 1.26(6H, d-t).

Mass (m/e): 417 (M+1).

The aldehyde compound can also be produced using the acetal compound as the starting material. In this method, the acetal compound represented by the general formula [XV] wherein $X_1$ is $N_3$, R' is $CH_3$ and $R_{31}$ is $^tBu$ [520 mg. (1.13 mmole)] obtained in Example 8-2, is dissolved in 10 ml of acetone and 50 mg. of the monohydrate of p-toluenesulfonate is added thereto. The mixture is stirred at room temperature for one hour and 45 minutes. To the reaction solution 20 ml of ethyl acetate is added and the mixture is washed with 5% aqueous sodium bicarbonate and saturated sodium chloride solution. The resulting solution is dried with anhydrous sodium sulfate and concentrated under reduced pressure to obtain 430 mg. (91.8%) of the aldehyde compound (Compound [XVI]').

(3) Preparation of Compound [XVII]', the thiophenyl compound represented by the general formula [XVII] wherein $X_1$ is $N_3$, $R_{11}$ is $SC_6H_5$ and $R_{31}$ is $^tBu$.

In this Example, 50% sodium hydride [120 mg. (2.5 mmole)] is added to a mixture of 970 mg. (8.8 mmole) of thiophenol and 6.5 ml of absolute ethanol. After the reaction of sodium hydride is completed, the reaction solution is cooled to a temperature of −78° C. on a dry ice-methanol bath, and 920 mg. (2.2 mmole) of the aldehyde compound (Compound [XVI]') which is obtained as above and dissolved in 6.5 ml of ethanol is added dropwise thereto in about 15 minutes.

The mixture is then stirred at a temperature of from −78° to −20° C. for 2 hours. Acetic acid and water are added to the mixture to raise the temperature to room temperature. The solution is then subjected to ether extraction and the ethyl layer is washed with saturated sodium chloride solution. The resulting solution is dried with anhydrous sodium sulfate and concentrated under reduced pressure to obtain 1.12 g of an oily product.

The product is charged on a column packed with 60 g of silica gel and elution is carried out with a solvent of n-hexane and ethyl acetate (2:1) whereby 470 mg. (40.4%) of the thiophenyl compound (the thiophenyl compound represented by the general formula [XVII] wherein $X_1$ is $N_3$, $R_{11}$ is $SC_6H_5$ and $R_{31}$ is $^tBu$) is obtained. Properties of the product are described below.

IR (CHCl$_3$) $\nu_{max}^{cm-1}$: 2120, 1780, 1735.

Mass (m/e): 526 (M+).

(4) Preparation of (±)-cis-2-t-butyloxycarbonyl-5-phenylthio-7-azido-1-azabicyclo [4, 2, 0] oct-2-en-8one (the cis-compound represented by the general formula [Ib] wherein $X_1$ is $N_3$, $R_{11}$ is $SC_6H_5$ and $R_{31}$ is $^tBu$ and represented by the following formula):

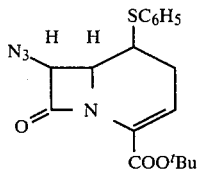

The thiophenyl compound (Compound [XVII)'] obtained in Example 8-3) [470 mg (0.89 mmole)] is dissolved in 14 ml of anhydrous dimethoxyethane and 47 mg (0.98 mmole) of 50% sodium hydride is added thereto. The mixture is stirred at room temperature for 3.5 hours and ether is added thereto. The mixture is washed with saturated aqueous ammonium chloride and saturated sodium chloride solution and dried with anhydrous sodium chloride. The resulting solution is concentrated under reduced pressure to obtain 340 mg of an oily product which is a mixture of stereoisomers at the 5-position of the desired compound.

The oily product is charged on a column packed with 15 g of silica gel and elution is carried out with a solvent of n-hexane and ethyl acetate (4:1, by volume) to obtain two isomers. These isomers have the following properties and are identified as the less polar isomer (configuration of proton at the 5-position is the same as those of protons at the 6- and 7-positions) of the desired compound, i.e., the cis compound represented by the general formula [Ib] wherein $X_1$ is $N_3$, $R_{11}$ is $SC_6H_5$ and $R_{31}$ is $^tBu$; and the more polar isomer (configuration of proton at the 5-position is the reverse of those protons at the 6- and 7-positions).

The less polar isomer A:

80 mg. (yield 9.7%, from Compound [XVI]').

IR (CHCl$_3$) $\nu_{max}^{cm-1}$: 2130, 1790, 1725, 1640.

NMR (CDCl$_3$)δ(ppm): 7.24–7.56(5H, m), 6.21(1H, d-d, J=3.0, 5,5 Hz), 5.06(1H, d, J=5 Hz), 3.65(1H, d-d, J=5, 11 Hz), 3.19(1H, d-d-d, J=5.5, 11, 11 Hz), 2.74(1H, d-d-d, J=5.5, 5.5, 19 Hz), 2.29(1H, d-d-d, =3, 11, 19 Hz), 1.50(s, 9H).

Mass (m/e): 372 (M+).

The more polar isomer B:

125 mg. (yield 15.2%, from Compound [XVI]')

IR (CHCl$_3$) $\nu_{max}^{cm-1}$: 2120, 1790, 1720, 1630.

Mass (m/e): 372 (M+).

NMR (CDCl$_3$)δ(ppm): 7.20–7.52(5H, m), 6.12(1H, d-d, J=3.5, 4.5 Hz), 4.98(1H, d, J=5 Hz), 3.99(1H, d-d, J=2.5, 5.0 Hz), 3.82(1H, m), 2.58–2.70(2H, m), 1.54(9H, s).

The less polar isomer can be also produced by the following method.

Sodium hydride [50% in oil dispersion, 56 mg. (1.16 mmole)] is added to a mixture of 440 mg. (4 mmole) of thiophenol and 3 ml of absolute ethanol. After reaction of sodium hydride is completed, the mixture is cooled to a temperature of −75° C. on dry ice-methanol bath. To the mixture, 440 mg. (1.06 mmole) of the aldehyde compound (Compound [XVI]') which is obtained as in Example 8-2, and dissolved in 3 ml of ethanol, is added dropwise. The mixture is stirred at a temperature of −75° C. for 50 minutes and acetic acid and water are added thereto to raise the temperature to room temperature. The resulting solution is then subjected to ether extraction. After washing with saturated sodium chloride solution, the extracts are dried with anhydrous sodium sulfate and the solvent is evaporated to obtain 595 mg. of a crude product. The product is dissolved in 15 ml of anhydrous dimethoxyethane and then 53 mg. (1.1 mmole) of 50% sodium hydride is added thereto. The solution is stirred at room temperature for one hour and 45 minutes and ether is added. After washing with saturated aqueous ammonium chloride and saturated sodium chloride solution, the solution is dried with anhydrous sodium sulfate and concentrated under reduced pressure to obtain 410 mg. of an oily product.

The oily product is charged on a column packed with 16 g of silica gel and elution is carried out with a solvent of n-hexane and ethyl acetate (4:1, by volume) whereby 100 mg. (25.4%) of the less polar isomer is obtained. Properties of the product agree with those of the less polar isomer mentioned above. In this case, no other polar isomer is obtained.

EXAMPLE 9

Preparation of (±)-cis-2-butyloxycarbonyl-5-phenylsulfinyl-7-azido-1-azabicyclo [4, 2, 0] oct-2-en-8-one, i.e., the cis-compound represented by the general formula [I] wherein X is $N_3$, $R_1$ is

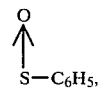

$R_2$ is H and $R_3$ is $^tBu$, represented by the general formula [Ie] wherein $X_1$ is $N_3$, $R_{12}$ is $C_6H_5$, Y is S and $R_3$ is $^tBu$, and represented by the following formula:

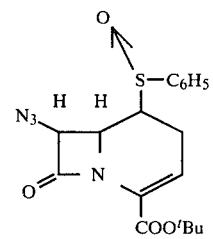

In this Example, 110 mg. (0.296 mmole) of (±)-cis-2-t-butyloxycarbonyl-5-phenylthio-7-azido-1-azabicyclo [4, 2, 0] oct-2-en-8-one which is the less polar isomer obtained in Example 8 is dissolved in 8 ml of methanol and 0.8 ml of benzene and then 140 mg. (0.655 mmole) of aqueous sodium periodate is added thereto. The mixture is stirred at room temperature for 60 hours. To the reaction mixture, water is added and then 15 ml of methylene chloride is added for extraction. The methylene chloride solution is dried over anhydrous magnesium sulfate and concentrated under reduced pressure to obtain 105 mg. of an oily product. Based on the following data, the product is identified as (±)-cis-2-t-butyloxycarbonyl-5-phenylsulfinyl-7-azido-1-azabicyclo [4, 2, 0] oct-2-en-8-one which is a mixture of two stereoisomers on the sulfur atom in the ratio of 1:1.

IR (CHCl$_3$) $\nu_{max}^{cm-1}$: 2130, 1790, 1725, 1640, 1050.

NMR (CDCl$_3$)δ(ppm): 7.55(5H, m), 6.30(1H, m), 5.27 (0.5H, d, J=5 Hz), 4.78(0.5H, d, J=5 Hz), 4.07(1H, d-d, J=5, 10 Hz), 2.40–3.00(2H, m).

EXAMPLE 10

Preparation of (±)-cis-2-carboxy-7-amino-1-azabicyclo [4, 2, 0] oct-2-en-8-one, i.e. the amino compound represented by the general formula [I] wherein X is NH$_2$, and R$_1$, R$_2$ and R$_3$ are H, and represented by the general formula [Ih] wherein R$_1$, R$_2$ and R$_3$ are H:

In this example, 91 mg. of (±)-cis-2-carboxy-7-azido-1-azabicyclo [4, 2, 0] oct-2-en-8-one, the compound represented by the general formula [If] wherein X is N$_3$, R$_2$ is H, and R$_1$ is H, obtained as in Example 3 is dissolved in 6.5 ml of ethanol and then 26 mg. of 10% palladium-carbon is added thereto. The mixture is stirred at room temperature and at atmospheric pressure in a stream of hydrogen for 2 hours. The mixture is then filtered to remove the catalyst and the filtrate is concentrated under reduced pressure. The concentrate is again dissolved in 10 ml of methanol and 26 mg. of 10% palladium-carbon is added. The mixture is subjected to catalytic reduction at room temperature and at atmospheric pressure for 3 hours and 50 minutes and is subjected to filtration using a filter aid, Hyflo Super Cel. The filtrate is concentrated under reduced pressure to obtain 88 mg. (100%) of a semi-solid product which is identified as the desired amino-compound based on the following data.

IR(KBr)$\nu_{max}^{cm-1}$: 3450, 2950, 1770, 1650.

EXAMPLE 11

Preparation of (±)-cis-7-amino-2-t-butyloxycarbonyl-1-azabicyclo [4, 2, 0] oct-2-en-8-one:

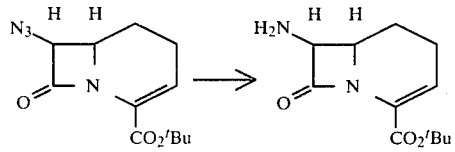

In this Example, 178 mg. (0.67 mmole) of (±)-cis-7-azido-2-t-butyloxycarbonyl-1-azabicyclo [4, 2, 0] oct-2-en-8-one obtained in Example 1 is dissolved in 10 ml of ethanol and 25 mg. of 10% palladium-carbon (catalyst) is added thereto. The mixture is stirred at room temperature in a stream of hydrogen for 50 minutes and then filtered to remove the catalyst. The filtrate is concentrated under reduced pressure to obtain 159.5 mg. of the desired compound as a yellow oily product. (Yield: 100%).

IR(CHCl$_3$)$\nu_{max}^{cm-1}$: 1775, 1725, 1640.

NMR (CDCl$_3$)δ(ppm): 6.27(m, 1H), 4.50(m, 1H), 4.2–3.1 (m, 3H), 2.6–1.7(m, 4H), 1.5(s, 9H).

EXAMPLE 12

Preparation of (±)-cis-2-t-butyloxycarbonyl-4-methyl-7-azido-1-azabicyclo [4, 2, 0] oct-2-en-8-one represented by the formula:

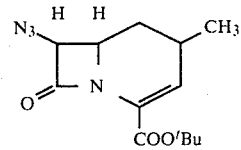

This compound may be produced by either of the following processes (1) and (2).

(1) Preparation of the t-butyl ester of 2-[4-(2-methyl-3-butenyl)-3-azido-2-oxoazetidin-1-yl]-2-diethylphosphonoacetate:

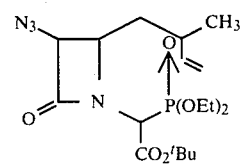

In this Example, 2.13 g (8 mmole) of t-butyl-α-amino diethylphosphonoacetate is dissolved in 80 ml of absolute ether and 902 mg. (9.2 mmole) of 3-methyl-4-pentenal is added with stirring. The mixture is stirred at room temperature for one hour and then 900 mg. of Molecular Sieve 4A and 700 mg. of magnesium sulfate are added thereto. The mixture is stirred for an additional 1.5 hours and is then filtered under reduced pressure. The filtrate is concentrated to obtain a pale yellow oily product. Then, 30 ml of anhydrous benzene is added and the mixture is again concentrated to obtain 2.82 g of an oily product. The presence of a Shiff's base is confirmed by NMR spectrum.

The oily product is dissolved in 56 ml of dried cyclohexane and 56 ml of anhydrous benzene, 900 mg. of Molecular Sieve 4A and 1.67 ml (12 mmole) of triethylamine are added thereto. Azidoacetylchloride [1.43 g (12 mmole)] dissolved in 56 ml of dried cyclohexane is added dropwise to the mixture with stirring at room temperature in 1.5 hours and the mixture is stirred for an additional 30 minutes. The reaction mixture is then transferred into a separatory funnel together with 30 ml of benzene. The benzene layer is washed with 30 ml portions of 10% citric acid, saturated sodium chloride solution, saturated sodium bicarbonate and saturated sodium chloride solution respectively. The resulting solution is dried with anhydrous sodium sulfate and concentrated under reduced pressure to obtain 2.8 g of an oily product. The presence of two isomers in the product is detected by thin layer chromatography [silica gel, n-hexane and ethyl acetate (1:1)].

The oily product is charged on a column packed with 300 g of silica gel and elution is carried out with n-hexane and ethyl acetate (1:1) whereby 380 mg. (yield 11.0%) of the less polar isomer of the desired compound, 570 mg. (yield 16.7%) of the more polar isomer, and 201 mg. (yield 5.8%) of a mixture of the two isomers are obtained. The properties of each of the isomers are set forth below from which the higher polar-isomer is identified as the cis isomer. The less polar-isomer (trans isomer):

IR(CHCl$_3$)$\nu_{max}^{cm-1}$: 2110, 1770, 1745.

NMR (CDCl$_3$)δ(ppm): 5.40–6.10(1H, m), 5.27–4.90(2.5H, m), 4.68(0.5H, d), 4.23(6H, m), 2.60–1.77(3H, m), 1.53 (9H, s), 1.37(6H, t, J=7.0 Hz), 1.10(3H, d, J=6.0 HZ).

The more polar isomer (cis isomer):

IR(CHCl$_3$)$\nu_{max}^{cm-1}$: 2110, 1765, 1745.

NMR(CDCl$_3$)δ(ppm): 5.45–6.13(1H, m), 4.83–5.20(2.5H, m), 4.67(0.5H, d), 3.97–4.45(6H, m), 1.77–2.55(3H, m), 1.50(9H, s), 1.33(6H, t), 1.08(3H, d).

(2) Preparation of (±)-cis-7-azido-2-t-butyloxycarbonyl-4-methyl-7-azido-1-azabicyclo [4, 2, 0] oct-2-en-8-one.

In this Example, 240 mg. (0.56 mmole) of the t-butylester of (±)-cis-2-[4-(2-methyl-3-butenyl)-3-azido-2-oxoazetidine-1-yl]-2-diethylphosphonoacetic acid obtained in Example (12-1) is dissolved in 6.6 ml of dioxane and 2 ml of deionized water and then 20 mg. of osmium tetroxide is added thereto. The mixture is stirred for 10 minutes and 390 mg. (1.82 mmole) of powdered sodium periodate is added in small portions to the black reaction mixture in 30 minutes. After stirring for 40 minutes, the reaction solution is extracted three times with 30 ml of ether. The extracted ether layers are combined, washed with saturated sodium chloride solution, dried with anhydrous sodium sulfate and concentrated to obtain 230 mg. of an oily product.

The oily product is charged on a column packed with 6 g of silica gel and elution is carried out with a solvent of benzene and ethyl acetate (1:2). Fractions which show a positive 2,4-dinitrophenylhydrazine reaction are combined and concentrated to obtain 185 mg. of an oily product which is the aldehyde of the desired compound. The product is immediately dissolved in 8 ml of anhydrous acetonitrile and 21.6 mg. (0.45 mmole) of 50% sodium hydride is added thereto at room temperature with stirring in a stream of nitrogen. After stirring for 30 minutes, the reaction mixture is poured into 15 ml of 2% aqueous acetic acid and the mixture is extracted twice with 20 ml of ether. The ether layers are washed with saturated sodium chloride solution, dried with anhydrous sodium sulfate and concentrated under reduced pressure to obtain an oily product.

The oily product is charged on a column packed with 20 g of silica gel and elution is carried out with a solvent of n-hexane and ethyl acetate (3.5:1, by volume), whereby 70 mg. of the desired product is obtained as a colorless oily product in a yield of 48.1%. The product crystallizes on standing. Properties of the product are as follows.

IR(KBr)$\nu_{max}^{cm-1}$: 2110, 1784, 1715, 1623.

NMR(CDCl$_3$)δ(ppm): 6.30(4/5H, d, J=5.1 Hz), 6.10(1/5H, d, J=2.7 Hz), 4.98(4/5H, d, J=5.0 Hz), 4.89(1/5H, d, J=5.0 Hz), 3.60–3.90(1H, m), 2.65(1H, m), 1.70–1.80(2H, m), 1.51(9H, s), 1.20(3/5H, d, J=8.0 Hz), 1.13 (12/5H, d, J=8.0 Hz)

Based on the NMR data, the crystals are identified as a mixture of the 4α-methyl isomer and the 4β-methyl isomer in a ratio of about 4:1. The compounds can be separated by silica gel chromatography using a solvent of n-hexane and ethyl acetate (3:1). The more polar isomer corresponds to the 4β-CH$_3$ isomer, i.e. (±)-cis-7β-azido-4β-methyl-2-t-butyloxycarbonyl-1-azabicyclo[4,2,0]oct-2-en-8-one and the less polar isomer corresponds to the 4α-CH$_3$ isomer. They have the following formulae and properties respectively.

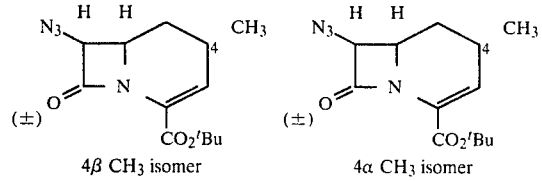

4β CH$_3$ isomer     4α CH$_3$ isomer

4β-CH$_3$ isomer

Melting point: 84.0°–86.5° C.

IR(KBr)$\nu_{max}^{cm-1}$: 2135, 1783, 1715, 1622.

NMR(CDCl$_3$)δ(ppm): 6.13(1H, d, J=2.7 Hz), 4.90(1H, d, J=5.0 Hz), 3.93–3.73(1H, m), 2.53(1H, m), 2.16–1.75 (2H, m), 1.53(9H, s), 1.20(3H, d, J=6.0 Hz).

4α-CH$_3$ isomer

Melting point: 82.0°–84.0° C.

IR(KBr)$\nu_{max}^{cm-1}$: 2120, 1790, 1721, 1630.

NMR(CDCl$_3$)δ(ppm): 6.33(1H, d, J=5.0 Hz), 5.00(1H, d, J=5.5 Hz), 3.89–3.68(1H, m), 2.66(1H, m) 1.82–1.57 (2H, m), 1.53(9H, s), 1.12(3H, d, J=7.0 Hz).

EXAMPLE 13

Preparation of (±)-cis-7β-amino-4α-methyl-2-t-butyloxycarbonyl-1-azabicyclo[4,2,0]oct-2-en-8-one:

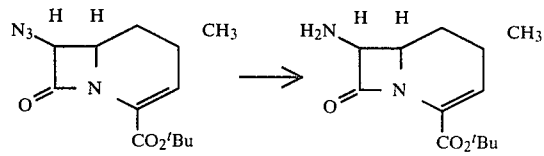

In this Example, 255 mg. (0.67 mmole) of (±)-cis-7β-azido-4α-methyl-2-t-butyloxycarbonyl-1-azabicyclo[4,2,0]oct-2-en-8-one obtained in Example (12-2) as a lower polar-isomer is dissolved in 10 ml of ethanol and 100 mg. of 10% palladium-carbon is added thereto. The mixture is subjected to catalytic hydrogenation for 1.5 hours and then is filtered to remove the catalyst. The catalyst is washed with methanol. The filtrate and the washings are combined and concentrated under reduced pressure to obtain a pale yellow oily product. The product is dissolved in 8 ml of ethyl acetate and the solution is extracted five times with 3 ml of 10% citric acid. The water layer is adjusted to a pH of 6 to 7 with potassium carbonate to obtain a white suspension. The suspension is then extracted twice with 5 ml of ethyl acetate and washed with saturated sodium chloride solution. The washings are dried with anhydrous sodium sulfate to obtain 177 mg. (76.6%) of an oily product having the following properties.

IR(CHCl$_3$)$\nu_{max}^{cm-1}$: 3400, 1770, 1720, 1630.

NMR(CDCl$_3$)δ(ppm): 6.23(1H, d, J=5.0 Hz), 4.53(1H, d, J=5.8 Hz), 3.93–3.47(1H, m), 2.56(1H, m), 1.92 (2H, br), 1.80–1.60(2H, m), 1.50(9H, s), 1.31 (3H, d, J=7.0 Hz).

EXAMPLE 14

Preparation of (±)-cis-7β-amino-4β-methyl-2-t-butyloxycarbonyl-1-azabicyclo[4,2,0]oct-2-en-8-one:

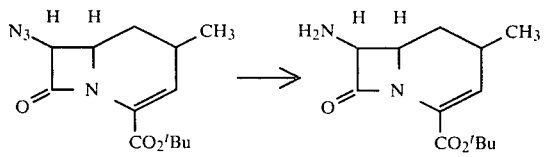

In this Example, 655 mg. (2.35 mmole) of (±)-cis-7β-azido-4β-methyl-2-t-butyloxycarbonyl-1-azabicyclo[4,2,0]oct-2-en-8-one obtained in Example (12-2) as a more polar isomer is dissolved in 6 ml of ethanol and 0.79 ml (2.37 mmole) of 3 N-HCl is added thereto. The mixture is subjected to hydrogenation with 200 mg. of 10% palladium-carbon for 70 minutes. Methanol is added to the resulting mixture to dissolve the deposited salt of the desired compound. The catalyst is removed by filtration and the filtrate is concentrated to obtain a crude product. The product is thoroughly triturated with ether and filtered. The filtrate is dried to obtain 512 mg. (75.4%) of the hydrochloride salt of the desired compound having the following properties.

Melting point: 216°–221° C. (dec.).

IR(KBr)$\nu_{max}^{cm-1}$: 3430, 2590, 1780, 1762, 1712, 1630.

EXAMPLE 15

Preparation of the trifluoroacetate of (±)-cis-7β-amino-4α-methyl-2-carboxy-1-azabicyclo[4,2,0]oct-2-en-8-one:

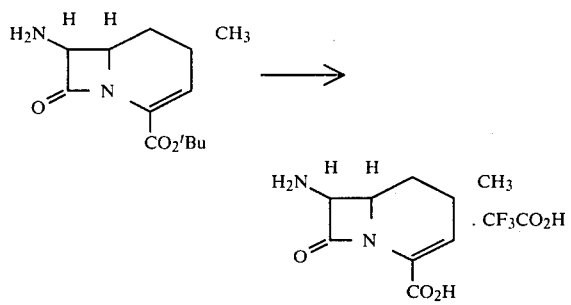

In this Example, 196 mg. (0.78 mmole) of (±)-cis-7β-amino-4α-methyl-2-t-butyloxycarbonyl-1-azabicyclo[4,2,0]oct-2-en-8-one obtained in Example 13 is dissolved in 4.2 ml of anhydrous dichloromethane and 1.8 ml of trifluoroacetic acid is added thereto at room temperature with stirring. After 1.5 hours, the mixture is concentrated under reduced pressure. The concentrate is subjected to azeotropic distillation with anhydrous benzene to obtain an oily product. The product is triturated with ether and filtered to obtain 167 mg. (69.3%) of a powder of the desired compound having the following properties.

IR(KBr)$\nu_{max}^{cm-1}$: 3460, 2980–2500, 1780, 1685, 1630.

PMR(D$_2$O, with DSS as an internal standard)δ(ppm): 6.77(1H, d, J=5.8 Hz), 5.00(1H, d, J=5.6 Hz), 4.10 (1H, m), 2.83(1H, m), 1.86(2H, m), 1.15(3H, d, J=8.0 Hz).

EXAMPLE 16

Preparation of (±)-cis-7β-amino-4α-acetoxy-1-azabicyclo [4, 2, 0] oct-2-en-8-one-2-carboxylic acid (1) Preparation of (±)-cis-7β-azido-4α-azetoxy-1-azabicyclo[4,2,0]oct-2-en-8-one-2-carboxylic acid:

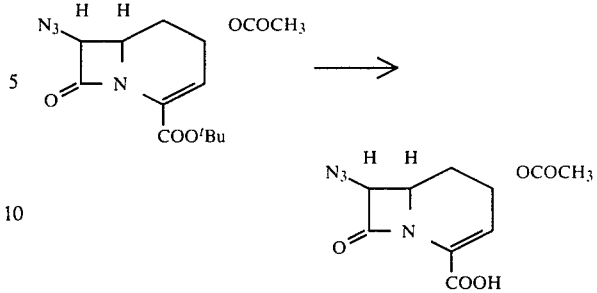

In this Example, 179 mg. of (±)-cis-7β-azido-4α-acetoxy-2-t-butyloxycarbonyl-1-azabicyclo[4,2,0]oct-2-en-8-one obtained as in Example 6 is dissolved in 3 ml of methylene chloride and 3 ml of trifluoroacetic acid. The solution is allowed to stand at room temperature for two hours and concentrated to obtain 145 mg. of the desired compound as a yellow powder. Yield 100%. Properties of the compound are as follows.

IR(CHCl$_3$)$\nu_{max}^{cm-1}$: 2130, 1790, 1715, 1445.

(2) Preparation of (±)-cis-7β-amino-4α-acetoxy-1-azabicyclo[4,2,0]oct-2-en-8-one-2-carboxylic acid:

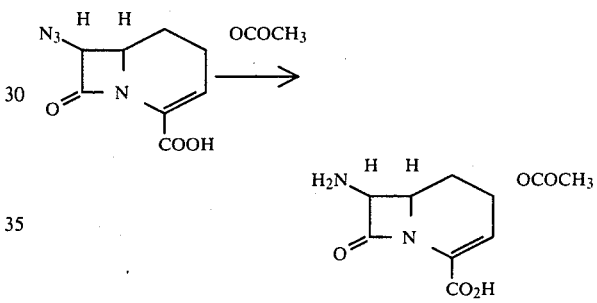

In this Example, 145 mg. of (±)-cis-7β-azido-4α-acetoxy-1-azabicyclo[4,2,0]oct-2-en-8-one-2-carboxylic acid obtained as in Example 6 is dissolved in 14 ml of ethanol and 40 mg. of 10% palladium-carbon is added thereto. The mixture is subjected to catalytic hydrogenation at atmospheric pressure with stirring for one hour. The reaction mixture is then filtered and the filtrate is concentrated to obtain 126 mg. of the desired compound.

EXAMPLE 17

Preparation of (±)-cis-7β-azido-2-t-butoxycarbonyl-4α-hydroxy-1-azabicyclo[4,2,0]oct-2-en-8-one, the cis compound represented by the general formula [I] wherein X is N$_3$, R$_1$ is H, R$_2$ is OH and R$_3$ is $^t$Bu represented by the formulas.

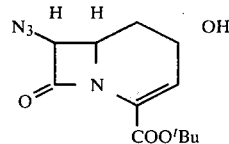

In this Example, 200 mg. of (±)-cis-2-t-butoxycarbonyl-7-azido-1-azabicyclo[4,2,0]oct-2-en-8-one obtained as in Example 1 is dissolved in 8.8 ml of carbon tetrachloride and 134.9 mg. of N-bromosuccinimide and a catalytic amount of α,α'-azobisisobutyronitrile is added.

The mixture is heated under reflux for 30 minutes. After cooling, the reaction mixture is diluted with 5 ml of chloroform and washed with 3 ml each of water and saturated sodium chloride solution. The washing is dried with anhydrous sodium sulfate and filtered. The filtrate is concentrated to obtain an oily bromo compound which is the same oily product obtained in Example 4. The product is immediately dissolved in 10 ml of acetone and 50 mg. of silver carbonate and 50 μl of water are added. The mixture is stirred at room temperature for 10 minutes. The reaction mixture is filtered and concentrated to obtain a crude product.

The crude product is charged on a column packed with 20 g of silica gel and elution is carried out with a mixture of n-hexane and ethyl acetate (2:1). The eluates are concentrated to obtain 86.4 mg. of the desired compound as pale yellow crystals having the following properties.

Yield 40.7%.
M.P.: 100.0°–101.0° C.
IR (CHCl$_3$) $v_{max}^{cm-1}$: 2130, 1790, 1635, 1630.
NMR (CDCl$_3$)δ(ppm): 6.30(1H, d, J=5 Hz), 5.03(1H, d, J=5.2), 4.47(1H, m), 3.93(1H, m), 3.20(1H, br), 2.1–1.8(2H, m), 1.55(9H, s).

EXAMPLE 18

Preparation of (±)-cis-7-amino-2-carboxy-1-azabicyclo[4,2,0]oct-2-en-8-one:

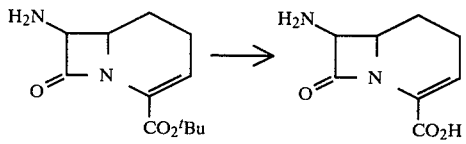

In this Example, 300 mg. of (±)-cis-7-amino-2-t-butyloxycarbonyl-1-azabicyclo[4,2,0]oct-2-en-8-one obtained as in Example 11 is dissolved in 3.0 ml of methylene chloride and 3.0 ml of trifluoroacetic acid is added. The mixture is allowed to stand at room temperature for one hour and 20 minutes. The reaction mixture is then concentrated and benzene is added to the residue. The solution is again concentrated to obtain 250 mg. of the trifluoroacetate of the desired compound as a yellow powder having the following properties.

IR (KBr)$v_{max}^{cm-1}$: 1780, 1680, 1630.

The above trifluoroacetate is dissolved in 2 ml of water and adjusted to pH 7.0 with saturated sodium bicarbonate to form crystals. Then, 129 mg. of the desired compound is recovered by filtration. Properties of the product agree with those of the product in Example 10.

EXAMPLE 19

Preparation of (±)-cis-7β-azido-2-carboxy-4α-methyl-1-azabicyclo[4,2,0]oct-2-en-8-one:

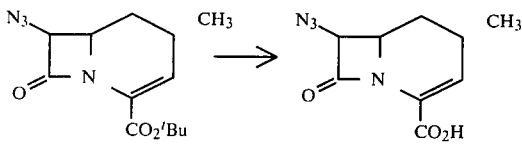

In this Example, 238 mg. (0.703 mmole) of (±)-cis-7β-azido-2-t-butyloxycarbonyl-4α-methyl-1-azabicyclo[4,2,0]oct-2-en-8-one obtained as in Example 12 is added 4 ml of trifluoroacetic acid and the mixture is allowed to stand at room temperature for 10 minutes. The reaction mixture is then concentrated at 25° C. under reduced pressure. The concentrate is extracted twice with 5 ml of dried benzene to obtain an oily product. Then, 255 mg. of the oily product is dissolved in 5 ml of ethyl acetate. The solution is extracted twice with 2 ml of 10% potassium carbonate and the water layer is adjusted to a pH of about 3 with 0.5 N HCl. The solution is extracted twice with 5 ml of ethyl acetate and dried over anhydrous sodium sulfate. The solvent is distilled off under reduced pressure to obtain 166 mg. of the desired compound as an oily product. Yield 83.8%. The product crystallizes on standing and has the following properties.

M.P.: 121.5°–123.0° C.
IR (CHCl$_3$)$v_{max}^{cm-1}$: 2110, 1769, 1750, 1716, 1630.
NMR (CD$_3$OD)δ(ppm): 6.47(1H, d, J=5.6 Hz), 5.22(1H, d, J=5.0), 4.2–3.7(1H, m), 2.3–2.9(1H, br), 1.11(3H, d, J=7.2).

EXAMPLE 20

Preparation of the trifluoroacetate of (±)-cis-7β-amino-2-carboxy-4α-methyl-1-azabicyclo[4,2,0]oct-2-en-8-one:

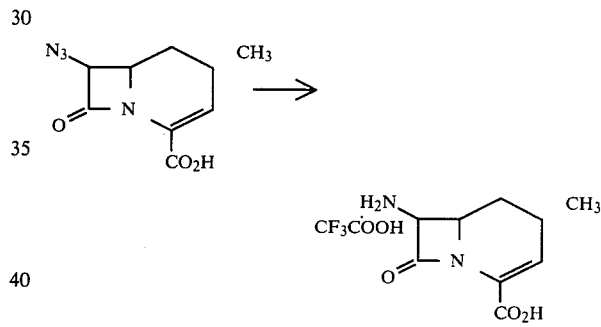

In this Example, 200 mg. of (±)-cis-7β-azido-2-t-butyloxycarbonyl-4α-methyl-1-azabicyclo[4,2,0]oct-2-en-8-one is dissolved in 2 ml of water and 2 ml of ethanol followed by addition of 75 mg. of 10% palladium-carbon. The mixture is stirred in a stream of hydrogen gas at atmospheric pressure. After 20 hours, the reaction mixture is filtered under reduced pressure. To the cake, 2 ml of trifluoroacetic acid is added.

After removing the catalyst by filtration, the filtrate is concentrated under reduced pressure followed by addition of 10 ml of dried ether. The crystals formed are recovered by filtration to obtain 120 mg. of the desired compound; Yield 43%. Properties of the compound agree with those in Example 15.

In the following Examples 21 to 40, the utility of compounds derived from Compound [I] as antimicrobial agents is illustrated.

EXAMPLE 21

Preparation of (±)-cis-2-carboxy-7-[2-thiophene-2-yl)acetylamino]-1-azabicyclo[4,2,0]oct-2-en-8-one represented by the following formula:

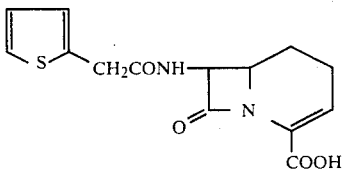

In this Example, 88 mg. (0.489 mmole) of the amino compound which is obtained in Example 10 and is represented by the general formula [I] wherein X is $NH_2$, and $R_1$, $R_2$ and $R_3$ are H is dissolved in 2 ml of deionized water and 1 ml of acetone and 84 mg. of aqueous sodium bicarbonate is added thereto. To the mixture, 78 mg. of 2-thienylacetylchloride dissolved in 0.5 ml of acetone is added dropwise under ice cooling. Then the mixture is stirred for 30 minutes and washed with ethyl acetate. The thus obtained aqueous layer is adjusted to a pH of 2.0 with hydrochloric acid, and the resulting white suspension is extracted three times with 5 ml of ethyl acetate. The ethyl acetate layer is washed with saturated sodium chloride solution, dried with anhydrous sodium sulfate and concentrated under reduced pressure to obtain a yellow oily product. The product is charged on a column packed with 4.0 g of silica gel and elution is carried out with chloroform. The thus obtained syrup is treated with chloroform-ethanol to obtain 30 mg. of crystalline product which is identified as the desired compound based on the following properties: Yield 20.1%.

Melting point: 181°–183° C.

IR(KBr)$\nu_{max}^{cm-1}$: 1775, 1690, 1650, 1615.

NMR(CD$_3$OD)$\delta$(ppm): 7.16–6.88(3H,m), 6.18(1H,t), 5.16(1H,d,J=5 Hz), 3.80(1H,m), 3.37(2H,s), 2.5–1.30(4H,m).

EXAMPLE 22

The antibacterial activity of ($\pm$)-cis-2-carboxy-7-[2-(thiophene-2-yl)acetylamino]-1-azabicyclo[4,2,0]oct-2-en-8-one obtained in Example 21 above is set forth below. The activity is determined by the regular agar dilution at pH 7.0.

| Microorganism | MIC ($\mu$g/ml) |
|---|---|
| Vibrio percolans KY4174 | 2 |
| Erwinia aroides KY3241 | 1 |
| Staphylococcus aureus KY4279 | 1 |
| Escherichia coli KY4271 | 8 |
| Bacillus subtilis KY4273 | 2 |
| Proteus vulgaris KY4277 | 8 |
| Shigella sonnei KY4281 | 8 |
| Salmonella typhosa KY4278 | 1 |
| Klebsiella penumoniae KY4275 | 4 |

EXAMPLE 23

Preparation of ($\pm$)-cis-7-[2-(2-tritylamino-4-thiazolyl)-2-anti-methoxyiminoacetamido]-2-t-butyloxycarbonyl-1-azabicyclo[4,2,0]oct-2-en-8-one:

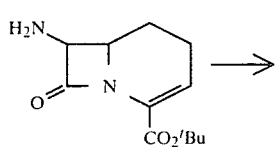

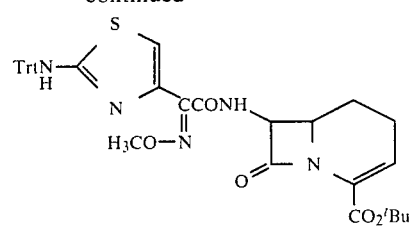

Method (a)

In this Example, 73 mg. (0.307 mmole) of ($\pm$)-cis-7-amino-2-t-butyloxycarbonyl-1-azabicyclo[4,2,0]oct-2-en-8-one obtained as in Example 11 and 135.9 mg. (0.307 mmole) of 2-(2-tritylamino-4-thiazolyl)-2-anti-methoxyiminoacetic acid are dissolved in 2 ml of anhydrous methylene chloride, and 69.6 mg. (0.307 mmole) of dicyclohexylcarbodiimide dissolved in 1 ml of anhydrous methylene chloride is added thereto with stirring under ice cooling. The mixture is stirred for three hours and is allowed to react at a temperature of 10° C. overnight. The reaction mixture is washed with 1% aqueous phosphate, saturated sodium bicarbonate and saturated sodium chloride solution. The washing is dried with magnesium sulfate and concentrated under reduced pressure to obtain 257 mg., of a crude product. The product is purified by column chromatography using 12 g of silica gel and a solvent of n-hexane and ethyl acetate (1:1) to obtain 73 mg. (35.9%) of the desired compound as a pale yellow glass having the following properties:

IR (KBr)$\nu_{max}^{cm-1}$: 1780, 1725, 1695(sh), 1690, 1635.

NMR(CDCl$_3$)$\delta$(ppm): 8.48(d,1H,J=6.4 Hz), 7.25(s,15H), 6.30(t,1H,J=3.0 Hz), 5.35(t,1H,J=6.4 Hz), 4.05 (s,3H), 2.5–1.6(m,4H), 1.52(s,9H).

Method (b)

In this Example, 524.9 mg (1.18 mmole) of 2-(2-tritylamino-4-thiazolyl)-2-anti-methoxyiminoacetic acid is dissolved in 10 ml of dried tetrahydrofuran. To the solution, 1.18 ml (1.18 mmole) of 1 N-N-methylmorpholine-tetrahydrofuran and 1.18 ml (1.18 mmole) of 1 N-isobutylchloroformate-tetrahydrofuran are added at a temperature of −30° C. and the mixture is stirred for 40 minutes. Then a solution of 235 mg. (0.987 mmole) of ($\pm$)-cis-7-amino-2-t-butyloxycarbonyl-1-azabicyclo [4,2,0]oct-2-en-8-one in 5 ml of anhydrous methylene chloride is added dropwise to the above mixture. The mixture is allowed to react for 30 minutes and is then stirred at 0° C. for 2 hours. To the reaction mixture, 10 ml of ethyl acetate is added and the mixture is washed with water, saturated sodium bicarbonate and saturated sodium chloride solution. The washing is dried with anhydrous sodium sulfate and concentrated under reduced pressure to obtain 865 mg. of a crude product. By silica gel chromatography using 40 g of silica gel according to Method (a), 580 mg. (87.5%) of the desired compound is obtained. The IR and NMR spectra of the product agree with those of compound prepared by Method (a).

EXAMPLE 24

Preparation of ($\pm$)-cis-7-[2-(2-amino-4-thiazolyl)-2-anti-methoxyimino-acetamido]-1-azabicyclo[4,2,0]oct-2-en-8-one-2-carboxylic acid:

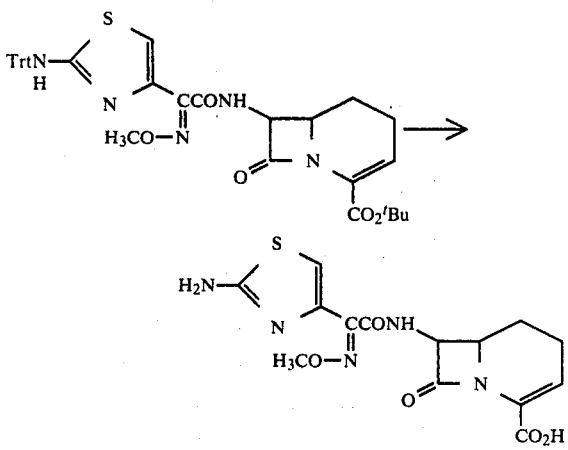

In this Example, 500 mg. (0.754 mmole) of (±)-cis-7-[2-(2-tritylamino-4-thiazolyl)-2-anti-methoxyiminoacetamido]-2-t-butyloxycarbonyl-1-azabicyclo[4,2,0]oct-2-en-8-one obtained in Example 23 is dissolved in a mixture of 5 ml of trifluoroacetic acid, 2.5 ml of anhydrous methylene chloride and 2.5 ml of anisole. The solution is allowed to stand at 0° C. for 3 hours and 40 minutes and is then concentrated under reduced pressure. To the concentrate, 5 ml of 50% aqueous acetic acid is added. The mixture is stirred at room temperature for 3 hours and is then concentrated under reduced pressure. The concentrate is thoroughly triturated with ether and filtered to obtain 244 mg. of a crude product. The product is purified by column chromatography with 10 ml of Diaion HP-10 (product of Mitsubishi Kasei Kogyo Co., Ltd.) and a solvent of methanol and water (2:5) to obtain 90 mg. (32.7%) of a pale yellow powder having the following properties.

IR(KBr)$\nu_{max}^{cm-1}$: 1760, 1670, 1630.
NMR(CD$_3$OD)$\delta$(ppm): 7.47(s,1H), 6.40(m,1H), 5.51(d,1H), J=5.0 Hz), 4.05(s,3H), 4.3–3.7(m,1H), 2.6–1.1(m,4H).

EXAMPLE 25

Preparation of (±)-cis-[(R)-2-phenyl-2-t-butyloxycarbonyl-aminoacetamido]-2-t-butyloxycarbonyl-1-azabicyclo[4,2,0]oct-2-en-8-one:

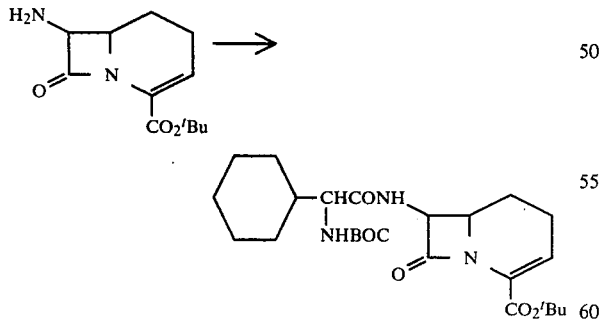

Method (a)
In this Example, 81 mg. (0.34 mmole) of (±)-cis-7-amino-2-t-butyloxycarbonyl-1-azabicyclo[4,2,0]oct-2-en-8-one and 94.0 mg. (0.34 mmole) of (R)-N-t-butyloxycarbonylphenylglycine are dissolved in 2 ml of anhydrous methylene chloride. A solution of 77 mg. (0.34 mmole) of dicyclohexylcarbodiimide in 1 ml of anhydrous methylene chloride is added to the solution under cooling with ice and sodium chloride. The mixture is allowed to react under cooling with ice for 2 hours and then two drops of acetic acid is added thereto. The mixture is stirred for 20 minutes and filtered under reduced pressure. The cake is washed with 20 ml of ethyl acetate. The filtrate and the washing are combined and 20 ml of ether is added thereto. The mixture is washed with 1% aqueous phosphoric acid, saturated sodium bicarbonate and saturated sodium chloride solution. The washing is dried with anhydrous sodium sulfate and concentrated under reduced pressure to obtain 187 mg. of a crude product. The product is purified by silica gel chromatography with 9 g of silica gel and a solvent of n-hexane and ethyl acetate (1:1) to obtain 104 mg. (64.9%) of the desired compound as a colorless glass having the following properties.

IR(KBr)$\nu_{max}^{cm-1}$: 1770, 1750, 1720, 1630
NMR(CDCl$_3$)$\delta$(ppm): 7.32(s,5H), 6.31(m,1H), 5.90(m,1H), 2.50–1.70(m,4H), 1.50(s,9H), 1.40(s,9H).

Method (b)
In this Example, 297.3 mg. (1.18 mmole) of (R)-N-t-butyloxycarbonylphenylglycine is dissolved in 5 ml of anhydrous tetrahydrofuran, and 1.18 ml (1.18 mmole) of 1N-N-methylmorpholine-tetrahydrofuran and 1.18 ml (1.18 mmole) of 1 N-i-Bu chloroformate-tetrahydrofuran are added at −30° C. The mixture is stirred for 30 minutes and 234 mg (0.983 mmole) of (±)-cis-7-amino-2-t-butyloxycarbonyl-1-azabicyclo[4,2,0]oct-2-en-8-one dissolved in 5 ml of anhydrous methylene chloride is added thereto. The mixture is allowed to react at a temperature of −30° C. for 45 minutes and at 0° C. for 4 hours and 15 minutes. The reaction mixture is then diluted with 15 ml of methylene chloride and is washed successively with water, 1 N-HCl, water and saturated sodium chloride solution. The washing is dried with anhydrous sodium sulfate and concentrated to obtain 588 mg. of a crude acyl-compound. Purification by silica gel chromatography with 28 g of silica gel is carried out according to Method (a) to obtain 322 mg. (69.4%) of the desired compound as a colorless glass. The IR and NMR spectra of the product agree with those of the compound prepared in Method (a).

EXAMPLE 26

Preparation of (±)-cis-7-[(R)-2-phenyl-2-aminoacetamido]-1-azabicyclo-[4,2,0]oct-2-en-8-on-2-carboxylic acid:

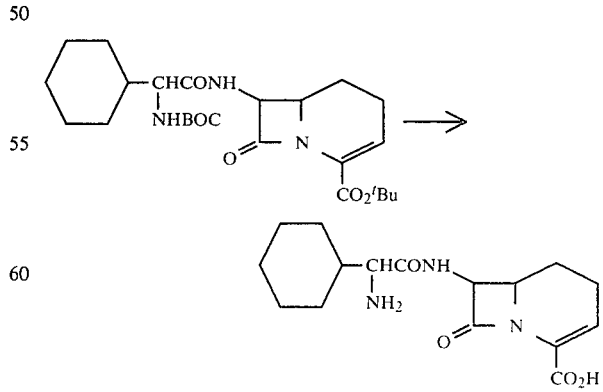

In this Example, 280 mg. (0.59 mmole) of (±)-cis-7-[(R)-2-phenyl-2-t-butyloxycarbonylaminoacetamido]-2-t-butyloxycarbonyl-1-azabicyclo[4,2,0]oct-2-en-8-one obtained in Example 25 is dissolved in 2.5 ml of anhydrous methylene chloride and 2.5 ml of anisole, and 5.0 ml of trifluoroacetic acid is added under ice cooling. The mixture is allowed to stand for 4 hours and 50 minutes under ice cooling and is then concentrated. To the concentrated residue, 10 ml of ether is added and the mixture is stirred at room temperature for one hour to form a precipitate. The precipitate is collected by filtration to obtain 202 mg. (70.9%) of the desired compound as a pale yellow powder having the following properties.

IR(KBr)$\nu_{max}^{cm-1}$: 1765, 1680, 1630

NMR(D$_2$O with DSS as an internal standard)$\delta$(ppm): 7.51(d,5H), 6.31(m,1H), 5.19(s,1H), 4.95(d,1H), 3.8–3.5(m, 1H), 2.6–2.9(m,4H)

Separation of the diastereoisomers of ($\pm$)-cis-7-[(R)-2-phenyl-2-aminoacetamido]-1-azabicyclo[4,2,0]oct-2-en-8-one-2-carboxylic acid:

The compound (50 mg.) obtained by the above method is dissolved in 150 ml of water and the solution is subjected to high speed liquid chromatography using Bondapak C-18 (product of Waters Co.) as a carrier and 7% methanol and 0.2 N potassium hydrogen phosphate as the solvent which is eluted eight times. The isolation of two fractions are monitored by a spectroscopic analysis at a wave length of 254 nm. After removing methanol under reduced pressure, each fraction is lyophilized. The dried matter is dissolved in water and adsorbed on a column packed with 20 ml of Diaion HP-10 (product of Mitsubishi Kasei Kogyo Co., Ltd.). The column is washed with 200 ml of water and elution is carried out with 20% ethanol. The fractions, positive to ninhydrin test are collected and lyophilized to obtain 14.0 mg. of A-isomer and 24.6 mg. of B-isomer as white powder. These are the potassium salts of the desired compound.

A: more polar fraction
[$\alpha$]$_D^{22°}$ (water, C=0.5): $-74.2°$.
IR (KBr)$\nu_{max}^{cm-1}$: 1750, 1690, 1640.
PMR(D$_2$O)$\delta$(ppm): 7.51(5H,s), 6.15(1H,t,J=3.9 Hz), 5.20(1H,d,J=4.9 Hz), 5.19(1H,s), 3.88(1H, octet, J=8.6, 3.7, 4.9 Hz), 2.41–1.41(4H,m).

B: less polar fraction
[$\alpha$]$_D^{22°}$ (H$_2$O, c=0.5): $+57.2°$.
IR(KBr)$\nu_{max}^{cm-1}$: 1760, 1690, 1640.
PMR(D$_2$O)$\delta$(ppm): 7.51(5H,s), 6.08(1H,t,J=4.2 Hz), 5.41(1H,d,J=4.9 Hz), 3.83(1H,octet,J=8.6, 3.7, 4.9 Hz), 2.28–1.01(4H,m).

Taking Structure Activity Relationship of cephalosporins into consideration, the less polar isomer which has dextro [$\alpha$]$_D$ value and stronger antimicrobial activity than the more polar isomer as shown in table below is assigned to have 6(R)7(S) absolute configuration.

EXAMPLE 27

Preparation of ($\pm$)-cis-7-[(R)-2-phenyl-2-(4-ethyl-2,3-dioxo-1-piperazinylcarbonylamino)-acetamido]-2-t-butyloxycarbonyl-1-azabicyclo[4,2,0]oct-2-en-8-one:

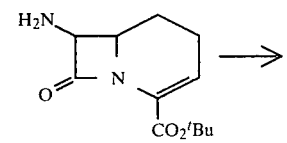

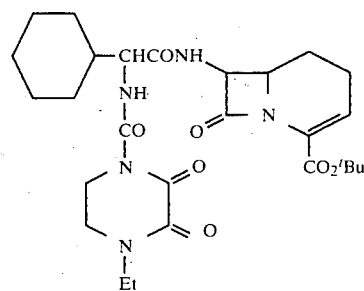

Method (a)

In this Example, 68 mg. (0.286 mmole) of ($\pm$)-cis-7-amino-2-t-butyloxycarbonyl-1-azabicyclo[4,2,0]oct-2-en-8-one and 100.4 mg. (0.286 mmole) of (R)-2-phenyl-2-(4-ethyl-2,3-dioxo-1-piperazinylcarbonylamino) acetic acid are dissolved in 2 ml of anhydrous methylene chloride, and 70 mg. (0.315 mmole) of dicyclohexylcarbodiimide dissolved in 1 ml of anhydrous methylene chloride is added under ice cooling. The mixture is stirred for 6 hours and then additionally stirred at a temperature of 10° C. overnight. The reaction mixture is filtered and the cake is washed with methylene chloride. The filtrate and the washing are combined and washed successively with 1% phosphoric acid, saturated sodium bicarbonate and saturated sodium chloride solution. The washing is dried with anhydrous sodium sulfate and concentrated to obtain 189 mg. of a crude acyl compound. The product is purified by silica gel chromatography using 9 g of silica gel and a solvent of n-hexane and ethyl acetate (1:2) to obtain 43 mg. of a more polar isomer, 20 mg. of a less polar isomer and 11.1 mg. of a mixture of the two isomers. The total yield is 54.1%.

The more polar isomer:
IR(CHCl$_3$)$\nu_{max}^{cm-1}$: 1780, 1720, 1695(sh), 1685.
NMR(CDCl$_3$)$\delta$(ppm): 7.73(d,1H,J=7.0 Hz), 7.37(s,5H), 6.25(m,1H), 5.7–5.0(m,2H), 4.3–3.0(m,7H), 2.6–0.7(m,4H), 1.50(s,9H), 1.20(t,3H).

The less polar isomer:
IR(CHCl$_3$)$\nu_{max}^{cm-1}$: 1780, 1695, 1685, 1620.
NMR(CDCl$_3$)$\delta$(ppm): 7.77(d,1H,J=8.0 Hz), 7.30(m,5H), 6.21(m,1H), 5.67–5.33(m,2H), 4.5–3.2(m,7H), 3.5–1.0(m,4H), 1.50(s,9H), 1.20(t,3H).

Method (b)

In this Example, 428.5 mg. (1.13 mmole) of (R)-2-phenyl-2-(4-ethyl-2,3-dioxo-1-piperazinylcarbonylamino) acetic acid is dissolved in 10 ml of dried tetrahydrofuran and 1.25 ml (1.25 mmole) of 1 N-N-methylmorpholinetetrahydrofuran and 1.25 ml (1.25 mmole) of 1 N-isobutylchloroformatetetrahydrofuran are added at a temperature of $-30°$ C. The mixture is stirred for 30 minutes and then 235 mg. (1.13 mmole) of ($\pm$)-cis-7-amino-2-t-butyloxycarbonyl-1-azabicyclo[4,2,0]oct-2-en-8-one dissolved in 5 ml of anhydrous methylene chloride is added. The mixture is allowed to react for one hour and is then stirred at a temperature of 10° C. overnight. The reaction mixture is diluted with 20 ml of ethyl acetate and washed successively with water, 0.1 N-HCl, saturated sodium bicarbonate and water. The washing is dried with anhydrous sodium sulfate and concentrated to obtain 570 mg. of a crude acyl compound. The product is purified and fractionated according to Method (a) except that 27 g of silica gel is used to obtain 73 mg. of a more polar isomer and 61 mg. of a less polar isomer (total yield 65.4%). The IR and NMR spectra of the isomers agree with those of the isomers obtained by Method (a).

EXAMPLE 28

Preparation of (±)-cis-7-[(R)-2-phenyl-2-(4-ethyl-2,3-dioxo-1-piperazinylcarbonylamino)acetamido]-1-azabicyclo[4,2,0]oct-2-en-8-one-2-carboxylic acid:

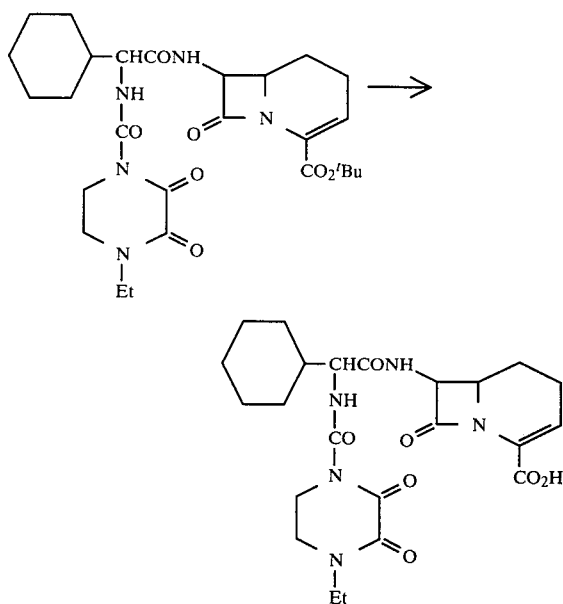

In this Example, 103 mg. (0.248 mmole) of (±)-cis-7-[(R)-2-phenyl-2-(4-ethyl-2,3-dioxo-1-piperazinyl-carbonylamino)acetamido]-2-t-butyloxycarbonyl-1-azabicyclo-[4,2,0]oct-2-en-8-one (the less polar isomer) obtained in Example 27 is dissolved in a mixture of 5 ml of trifluoroacetic acid, 5 ml of methylene chloride and two drops of anisole. The mixture is allowed to react at 0° C. for 2 hours and is then concentrated under reduced pressure. To the concentrate, dried benzene is added and the mixture is again concentrated to obtain an oily product. To the product, ether is added and the mixture is stirred at room temperature to form a yellow precipitate. The crude product (104 mg.) is collected by filtration as a yellow powder. The crude product is then dissolved in ethyl acetate and extracted with 5 ml of saturated sodium bicarbonate three times. The extracts are washed with ethyl acetate. The washing is adjusted to a pH of 2.5 with 0.5 N-HCl under ice cooling and extracted with 5 ml of ethyl acetate three times. The extract is washed with saturated sodium chloride solution, dried with magnesium sulfate, and concentrated under reduced pressure to obtain 41 mg. (46.0%) of a pale yellow powder having the following properties.

IR(KBr)$\nu_{max}^{cm-1}$: 1775, 1720, 1685, 1620(sh).

NMR(CD$_3$OD)δ(ppm): 7.31(s,5H), 6.33(t,1H,J=4.0 Hz), 5.40(m,2H), 4.30–3.1(m,7H), 2.40–0.7(m,4H), 1.27(t,3H).

From strong antimicrobial activity as shown in table below, this compound is assigned to have 6(R)7(S) absolute configuration.

EXAMPLE 29

Preparation of (±)-cis-7β-[(R)-2-phenyl-2-t-butyloxycarbonylaminoacetamido]-4β-methyl-2-t-butyloxycarbonyl-1-azabicyclo[4,2,0]oct-2-en-8-one:

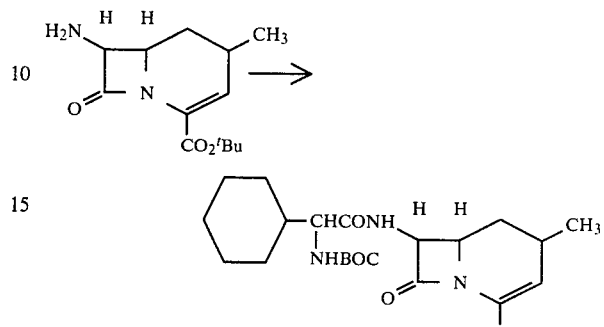

In this Example, 132 mg. (0.53 mmole) of (R)-N-t-butyloxycarbonylphenylglycine is dissolved in 5 ml of anhydrous tetrahydrofuran, and 0.53 ml (0.53 mmole) of 1 N-N-methylmorpholine and 0.53 ml (0.53 mmole) of 1 N-isobutyl chloroformate are added thereto at a temperature of 0° C. The mixture is stirred for 15 minutes and 0.07 ml (0.5 mmole) of triethylamine and 1.44 mg. (0.5 mmole of the hydrochloride of (±)-cis-7β-amino-4β-methyl-2-t-butyloxycarbonyl-1-azabicyclo[4,2,-0]oct-2-en-8-one obtained in Example 14 are added thereto. The mixture is stirred at a temperature of 0° C. for one hour and then at a temperature of 5° to 10° C. overnight.

The reaction mixture is diluted with 10 ml of ethyl acetate and washed successively with 10% citric acid, saturated sodium bicarbonate, and saturated sodium chloride solution. The washing is dried with anhydrous sodium sulfate and concentrated to obtain a crude acyl compound. The product is purified by column chromatography using 30 g of silica gel and a solvent of n-hexane and ethyl acetate (3:1, by volume) whereby 150 mg. (61.7%) of the desired compound is obtained as a powder having the following properties.

IR(KBr)$\nu_{max}^{cm-1}$: 3290, 1780, 1720, 1685, 1665.

NMR(CDCl$_3$)δ(ppm): 7.34(5H,s), 6.60, 6.49(1H,d respectively, J=7 Hz), 6.11, 6.04(1H,d respectively J=2 Hz), 5.66, 5.60(1H,d, respectively, J=7 Hz), 5.18(2H,m), 3.86(1H,m), 2.46(1H,m), 1.75(2H,br), 1.51(9H,s), 1.42(9H,s), 1.15, 0.98(3H,d respectively, J=7.5 Hz).

EXAMPLE 30

Preparation of the trifluoroacetate of (±)-cis-7β-[(R)-2-phenyl-2-aminoacetamido]-4β-methyl-2-carboxy-1-azabicyclo[4,2,0]oct-2-en-8-one:

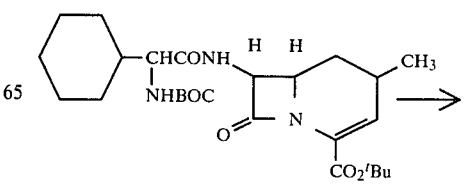

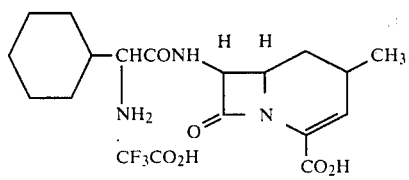

In this example, 100 mg. (0.21 mmole) of (±)-cis-7β-[(R)-2-phenyl-2-t-butyloxycarbonyl-aminoacetamido]-4β-methyl-2-t-butyloxycarbonyl-1-azabicyclo[4,2,0]oct-2-en-8-one obtained in Example 29 is dissolved in 1 ml of anhydrous methylene chloride and 1 ml of trifluoroacetic acid is added thereto under cooling on an ice bath. The mixture is allowed to stand at a temperature of 0° to 5° C. for 3.5 hours with occasional shaking. The reaction mixture is then concentrated under reduced pressure. The concentrate is triturated with 5 ml of anhydrous ethyl ether and the ether layer is removed by decantation. The treatment is repeated three times and the resulting cake is dried under reduced pressure to obtain 70 mg. (75%) of the desired compound as a powder having the following properties.

IR(KBr)$\nu_{max}^{cm-1}$: 3450(sh), 3230(sh), 3060, 2960–2800, 1769, 1695(sh), 1681(sh), 1673.

NMR(DMSO-$d_6$)δ(ppm): 9.29(1H,t,J=8 Hz), 7.49(5H,s), 6.11, 6.04(1H,d respectively, J=2 Hz), 5.30(1H, m), 4.97(1H,d,J=4 Hz), 3.82(1H,br), 2.44(br, partly overlapping with the signal of DMSO-$d_6$), 1.82(2H,br), 1.14, 0.91(3H,d, respectively, J=7.5 Hz).

EXAMPLE 31

Preparation of (±)-cis-7β-[(R)-2-phenyl-2-t-butyloxycarbonyl-acetamido]-4α-methyl-2-t-butyloxycarbonyl-1-azabicyclo[4,2,0]oct-2-en-8-one:

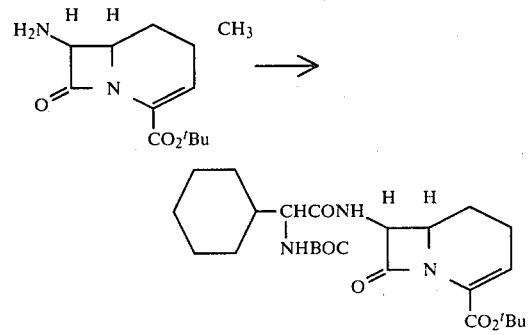

In this Example, the same procedure as in Example 29 is employed except that 144 mg. of (±)-cis-7β-amino-4α-methyl-2-t-butyloxcarbonyl-1-azabicyclo[4,2,0]oct-2-en-8-one obtained in Example 13 is used as a starting compound. As a result, 140 mg. (57.6%) of the desired compound is obtained having the following properties.

IR(KBr)$\nu_{max}^{cm-1}$: 3330, 1792(sh), 1782, 1730, 1692, 1675.

NMR(CDCl$_3$)δ(ppm): 7.34(5H,s), 6.73, 6.60(1H, d respectively, J=7 Hz), 6.28(1H,t,J=6 Hz), 5.60(1H, m), 5.43–5.18(2H,m), 3.82(1H,m), 2.55(1H,m), 1.69(2H,m), 1.51(9H,s), 1.41(9H,s), 1.09, 1.03 (3H,d respectively, J=7 Hz).

EXAMPLE 32

Preparation of (±)-cis-7β-[(R)-2-phenyl-2-aminoacetamido]-4α-methyl-2-carboxy-1-azabicyclo[4,2,0]oct-2-en-8-one:

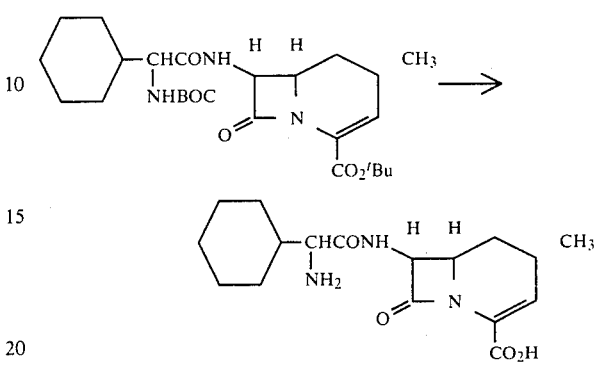

In this Example, the same procedure as in Example 30 is employed except that 80 mg. of (±)-cis-7β-[(R)-2-phenyl-2-t-butyloxycarbonyl-aminoacetamido]-4α-methyl-2-t-butyloxycarbonyl-1-azabicyclo[4,2,0]oct-2-en-8-one obtained in Example 31 is used as a starting compound. As a result, 73 mg. (100%) of the desired compound is obtained having the following properties.

IR(KBr)$\nu_{max}^{cm-1}$: 3430, 3200, 3060, 2960–2650, 1780(sh), 1770, 1695(sh), 1680.

NMR(DMSO-$d_6$)δ(ppm): 9.36(1H,d,J=8 Hz), 7.47(5H,s), 6.28(1H,d,J=6 Hz), 5.40(1H,m), 4.98(1H,m), 3.70 (1H,br), 2.45(br, partly overlapping with the signal of DMSO-$d_6$), 1.80(2H,m), 1.06, 0.95(3H,d respectively, J=7.5 Hz).

EXAMPLE 33

Preparation of (±)-cis-7β-[2-(2-tritylamino-4-thiazolyl-2-methoxyiminoacetamido]-4α-methyl-2-t-butyloxycarbonyl-1-azabicyclo[4,2,0]oct-2-en-8-one:

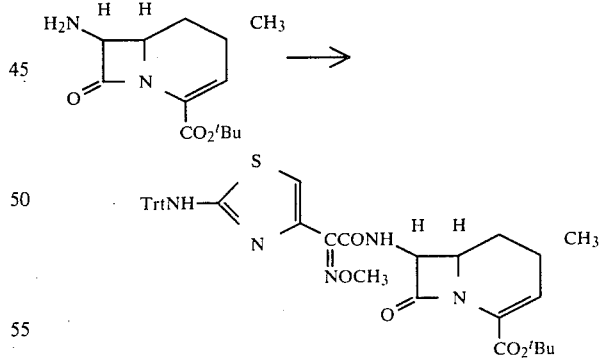

Method A

In this Example, 88 mg. (0.35 mmole) of (±)-cis-7β-amino-4α-methyl-2-t-butyloxycarbonyl-1-azabicyclo[4,2,0]oct-2-en-8-one is dissolved in 1.5 ml of anhydrous methylene chloride and 155 mg. (0.35 mmole) of 2-(2-tritylamino-4-thiazolyl)-2-anti-methoxyiminoacetic acid is added. Then, 1.5 ml of anhydrous dioxane is added to the mixture to make it more homogeneous. To the mixture, 80 mg. (0.39 mmole) of dicyclohexylcarbodiimide dissolved in 1 ml of dioxane is added and the resulting mixture is stirred at a temperature of 5° to 10°

C. overnight. The resulting white precipitate is filtered off and 10 ml of ethyl acetate and 5 ml of ether are added to the filtrate. The mixture is washed with 5 ml of 1% cold phosphoric acid three times and then saturated sodium bicarbonate. The washing is dried with anhydrous sodium sulfate and concentrated under reduced pressure to obtain 290 mg. of the crude desired compound as a semisolid. The crude compound is charged on column packed with 27 g of silica gel and elution is carried out with n-hexane and ethyl acetate (2:1). The eluate is concentrated under reduced pressure to obtain 170 mg. (72%) of the desired compound having the following properties.

Melting point (recrystallized from n-hexane and ethyl acetate): 214.5°–215.5° C.

IR(KBr)$\nu_{max}^{cm-1}$: 3240, 1780(sh), 1762, 1730, 1665, 1636.

NMR(CDCl$_3$-CD$_3$OD)δ(ppm): 7.30(15½ H,s), 6.64(⅜H,s), 6.34(1H,d,J=7 Hz), 5.48(⅜H,d,J=5.5 Hz), 5.43(⅛H,d,J=5.5 Hz), 4.08(1H,s), 4.01(2H,s), 3.90(1H,m), 2.66(1H,m), 1.75(2H,m), 1.54(3H,s), 1.53(6H,s), 1.14(3H,d,J=7 Hz).

Method B

In this Example, 243.9 mg. (0.05 mmole) of 2-(2-tritylamino-4-thiazolyl)-2-anti-methoxyiminoacetic acid is dissolved in 5 ml of anhydrous tetrahydrofuran and 0.55 ml (0.55 mmole) of 1 N-N-methylmorpholine is added. To the mixture, 0.55 ml (0.55 mmole) of 1 N-i-Bu chloroformatetetrahydrofuran is added dropwise at a temperature of 0° C. with stirring and the mixture is then additionally stirred for 15 minutes. Triethylamine [0.11 ml (0.5 mmole)] is added to the mixture followed by addition of 144 mg. (0.5 mmole) of the hydrochloride of (±)-cis-7β-amino-4α-methyl-2-t-butyloxycarbonyl-1-azabicyclo[4,2,0]oct-2-en-8-one. The mixture is stirred at a temperature of 5° to 10° C. overnight and concentrated under reduced pressure. Then 10 ml of ethyl acetate is added to the concentrate and the resulting mixture is washed successively with 5% hydrochloric acid, saturated sodium chloride solution, saturated sodium bicarbonate and saturated sodium chloride solution. The washing is dried with anhydrous sodium sulfate and concentrated under reduced pressure to obtain a crude product. The crude product is charged on a column packed with 25 g of silica gel and elution is carried out with n-hexane and ethyl acetate (5:3). The eluate is concentrated under reduced pressure to obtain 250 mg. (74.0%) of the desired compound, the physical properties of which agree with those of the compound prepared by Method A.

EXAMPLE 34

Preparation of (±)-cis-7β[2-(2-amino-4-thiazolyl)-2-anti-methoxyiminoacetamido]-4α-methyl-2-carboxy-1-azabicyclo[4,2,0]oct-2-en-8-one:

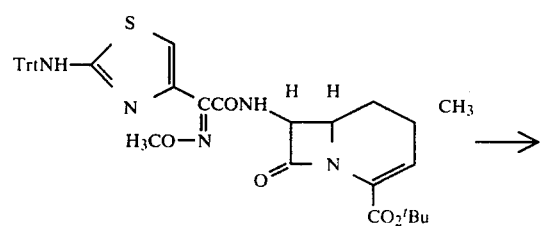

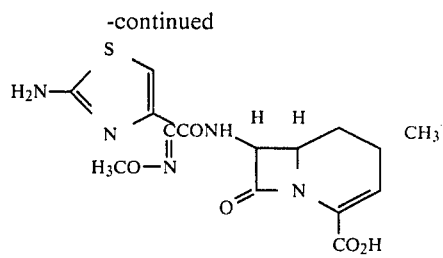

In this Example, 70 mg. (0.103 mmole) of (±)-cis-7β-[2-(2-tritylamino-4-thiazolyl)-2-anti-methoxyiminoacetamido]-4α-methyl-2-butyloxycarbonyl-1-azabicyclo[4,2,0]oct-2-en-8-one obtained in Example 33 is dissolved in 0.5 ml of anhydrous methylene chloride and 0.1 ml of anisole. The mixture is cooled to 0° C. followed by addition of 0.5 ml of trifluoroacetic acid. The resulting mixture is allowed to stand on an ice bath for 3.5 hours.

The reaction mixture is then concentrated under reduced pressure. The concentrate is triturated with 5 ml of anhydrous ethyl ether and filtered to obtain a white powder. The powder is dissolved in 2 ml of 50% acetic acid. The solution is allowed to stand at room temperature for 2.5 hours and then at a temperature of 5° to 10° C. overnight. The solution is then allowed to stand at room temperature (25° C.) for 6 hours and concentrated under reduced pressure to obtain a glassy product. The glassy product is thoroughly triturated with ether and filtered. The filtrate is dried to obtain 20 mg. (51%) of the desired compound having the following properties.

IR(KBr)$\nu_{max}^{cm-1}$: 3480, 3300, 1770, 1680, 1635.

NMR(DMSO-d$_6$)δ(ppm): 9.17(1H,d,J=8 Hz), 7.50(1H,s), 7.24(2H,m), 6.31(1H,d,J=6 Hz), 5.52(1H,m), 4.00(3H,s), 2.65(br, partly overlapping with the signal of DMSO-d$_6$), 1.70(2H,m), 1.06(3H,d, J=7.5 Hz).

EXAMPLE 35

Preparation of (±)-cis-7β-[2-(2-tritylamino-4-thiazolyl)-2-methoxyiminoacetamido]-4β-methyl-2-t-butyloxycarbonyl-1-azabicyclo[4,2,0]oct-2-en-8-one:

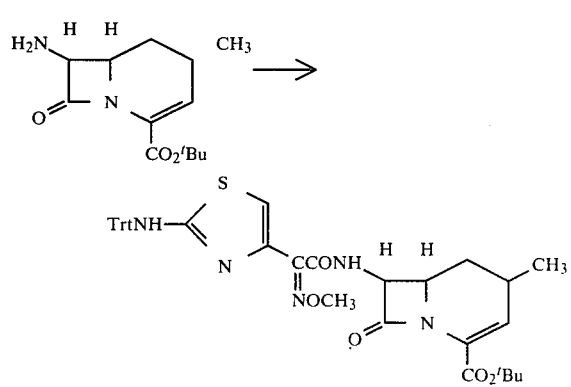

In this Example, the same procedure as in Example 33, Method B, is employed except that 202 mg. (0.7 mmole) of (±)-cis-7β-amino-4β-methyl-2-t-butyloxycarbonyl-1-azabicyclo[4,2,0]oct-2-en-8-one is used as a starting compound. As a result, 251 mg. (53%) of the desired compound is obtained having the following properties.

Melting point: 201.0°–202.0° C.

IR(KBr)$\nu_{max}{}^{cm-1}$: 3225, 1780(sh), 1760, 1725, 1668, 1635.

NMR(CDCl$_3$-CD$_3$OD)δ(ppm): 7.35($\frac{1}{2}$H,s), 7.30(15H, s), 6.65($\frac{1}{2}$H,s), 6.14(1H,d,J=2 Hz), 5.38(1H,d-d, J=5 Hz), 4.09(3/2H,s), 4.01(3/2H,s), 3.96(1H,m), 2.45(1H,m), 2.05(2H, m), 1.53(9/2H,s), 1.52(9/2H, s), 1.16(3H,d-d,J=7.5 Hz).

EXAMPLE 36

Preparation of (±)-cis-7β-[2-(2-amino-4-thiazolyl)-2-methoxyiminoacetamido]-4β-methyl-2-carboxy-1-azabicyclo[4,2,0]oct-2-en-8-one:

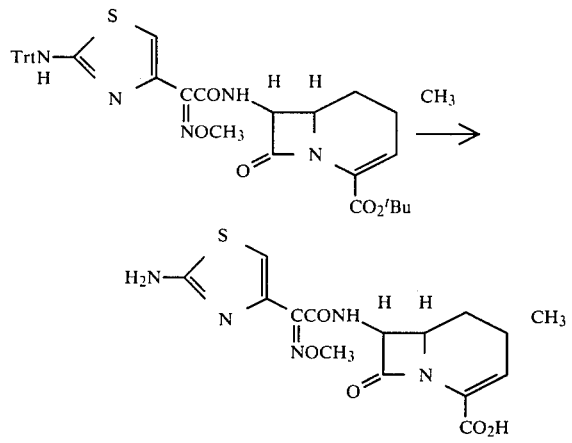

In this Example, the same procedure as in Example 34 is employed except that 70 mg. of (±)-cis-7β-[2-(2-tritylamino-4-thiazolyl)-2-methoxyiminoacetamido]-4β-methyl-2-t-butyloxycarbonyl-1-azabicyclo[4,2,-0]oct-en-8-one obtained in Example 35 is used as a starting compound. As a result, 22 mg. (56%) of the desired compound is obtained having the following properties.

IR(KBr)$\nu_{max}{}^{cm-1}$: 3460, 3280, 1780(sh), 1770, 1670, 1630.

NMR(DMSO-d$_6$)δ(ppm): 9.24($\frac{1}{2}$H,d,J=8 Hz), 9.17($\frac{1}{2}$H,d, J=8 Hz), 7.50($\frac{1}{2}$H,s), 7.25(2H,m), 6.78($\frac{1}{2}$H,s), 6.10(1H,d,J=2 Hz), 5.47(1H,m), 4.00(3/2H,s), 3.85(3/2H,s), 2.60(br, partly overlapping with the signal of DMSO-d$_6$), 1.91(2H,m), 1.12(3H, d-d,J=7.5 Hz).

EXAMPLE 37

Preparation of (±)-cis-7β-[2-(2-chloroacetylamino-4-thiazolyl)-2-syn-methoxyiminoacetamido]-4α-methyl-2-carboxy-1-azabicyclo[4,2,0]oct-2-en-8-one:

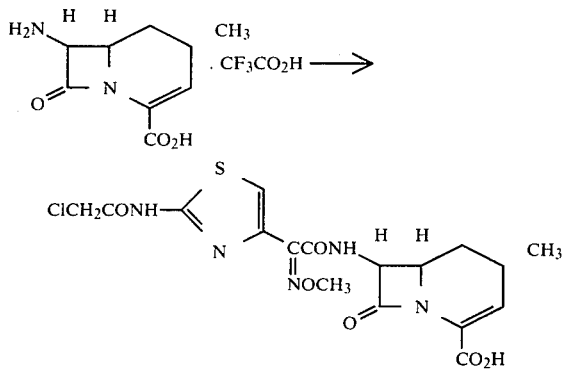

In this Example, 172 mg. (0.62 mmole) of (2-chloroacetylamino-4-thiazolyl)-2-syn-methoxyiminoa- cetic acid is suspended in 3.6 ml of anhydrous dichloromethane and 68.9 mg. (0.68 mmole) of triethylamine is added thereto to make the solution homogeneous. Under cooling on an ice-sodium chloride bath, 129 mg. (0.62 mmole) of phosphorous pentachloride is added to the mixture with stirring and the resulting mixture is stirred for 1.5 hours. Then 13.8 ml of n-hexane is added to the mixture and the supernatant is removed by decantation. Anhydrous tetrahydrofuran (1.3 ml) is added to the residue to obtain an acid chloride solution.

On the other hand, 160 mg. (0.52 mmole) of the trifluoroacetate of (±)-cis-7β-amino-4α-methyl-2-carboxy-1-azabicyclo[4,2,0]oct-2-en-8-one obtained in Example 35 is dissolved in 1 ml of 50% tetrahydrofuran-water, and 209 mg. (2.06 mmole) of triethylamine is added thereto. The mixture is added to the acid chloride solution under ice cooling with stirring. After stirring at the same temperature for 1.5 hours, the mixture is adjusted to a pH of 4 to 5 with 1 N-hydrochloric acid and extracted with 10 ml of ethyl acetate three times. The ethyl acetate extracts are washed with sodium chloride solution, dried with anhydrous sodium sulfate and concentrated under reduced pressure to obtain 417 mg. (52.1%) of the desired compound having the following properties.

IR(KBr)$\nu_{max}{}^{cm-1}$: 1765, 1680.
PMR(DMSO-d$_6$)δ(ppm): 7.40(1H,s), 6.32(1H,d,J=5.2 Hz) 5.53(1H,m), 4.35(2H,s), 3.90(3H,s), 2.50(1H,m), 1.90–1.27(2H,m), 1.10(3H,d,J=7.5 Hz).

EXAMPLE 38

Preparation of (±)-cis-7β-[2-(2-amino-4-thiazolyl)-2-syn-methoxyiminoacetamido]-4α-methyl-1-azabicyclo[4,2,0]oct-2-en-8-one-2-carboxylic acid:

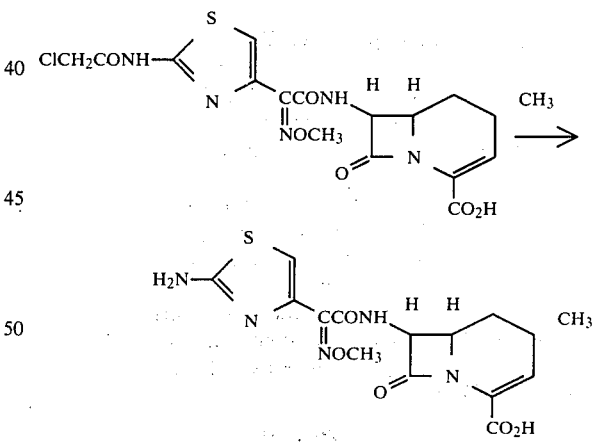

In this Example, 147 mg. (0.321 mmole) of the chloroacetyl compound obtained in Example 37 is dissolved in 0.5 ml of dimethylsulfoxide and 2.5 ml of dimethylformamide and 47 mg. (0.64 mmole) of thiourea is added thereto at room temperature with stirring. The mixture is stirred for 14 hours. After addition of ether, the supernatant is removed by decantation and the residue is dissolved in a small amount of dimethylsulfoxide. The solution is then adsorbed on a column packed with 10 ml of Diaion HP-10. The column is washed with 240 ml of water and elution is carried out with a solvent of methanol and water (1:10 to 1:2). The eluate is collected and methanol is removed under reduced pressure. The residue is again adsorbed on a column packed with 10 ml of Diaion HP-10 and the column is washed with 500 ml of water. Elution is then carried out with a solvent of methanol and water (1:1). The eluate is collected and concentrated under reduced pressure to obtain 50.2 mg. (41.1%) of the desired compound having the following properties.

IR(KBr)$\nu_{max}^{cm-1}$: 1760, 1680, 1655.

PMR(DMSO-d$_6$)δ(ppm): 9.27(1H,d,J=9.0 Hz), 7.15(2H,br), 6.75(1H,s), 6.31(1H,d,J=4.2 Hz), 5.58(1H,br), 3.85(3H,s), 2.60(1H,m), 1.67(2H,br), 1.08(3H,d, J=8 Hz).

EXAMPLE 39

Preparation of (±)-cis-7-[2-(2-chloroacetylamino-4-thiazolyl)-2-syn-methoxyiminoacetamid]-1-azabicyclo[4,2,0]oct-2-en-8-on-2-carboxylic acid:

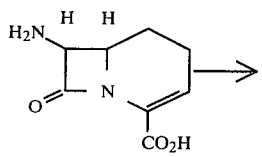

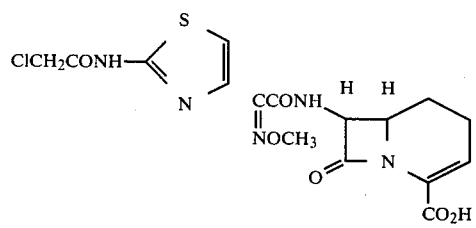

In this Example, 54.2 mg. (0.195 mmole) of 2-chloroacetylamino-4-thiazolyl-2-syn-methoxyiminoacetic acid is suspended in 0.98 ml of anhydrous methylene chloride and 23.48 mg. (0.195 mmole) of triethylamine is added. Phosphorus pentachloride 40.8 mg. (0.195 mmole) is added to the reaction mixture under ice cooling. After stirring for 20 minutes, 3.92 ml of n-hexane is added to the mixture and the supernatant is removed by decantation. The residue is dissolved in 1.96 ml of tetrahydrofuran to obtain an acid chloride solution.

On the other hand, 45.9 mg. (0.155 mmole) of the trifluoroacetate of (±)-cis-7-amino-2-carboxy-1-azabicyclo[4,2,0]oct-2-en-8-one obtained in Example 10 is dissolved in 2 ml of 50% tetrahydrofuran-water and 47.4 mg. (0.469 mmole) of triethylamine is added thereto. To this solution, the above acid chloride solution is added under ice cooling and the mixture is stirred for 2 hours. The mixture is then adjusted to a pH of 2.0 with 10% hydrochloric acid and extracted three times with ethyl acetate. The extracts are washed with saturated sodium chloride solution. The washing is dried with anhydrous sodium sulfate and concentrated to obtain 80 mg. of the desired compound as a pale yellow powder having the following properties.

IR(KBr)$\nu_{max}^{cm-1}$: 1760, 1710, 1660.

PMR(DMSO-d$_6$)δ(ppm): 16.64(1H,br), 9.39(1H,d,J=8.8 Hz), 7.47(1H,s), 6.31(1H,t), 5,51(1H,d-d,J=5.5, 8.8 Hz), 4.38(2H,s), 3.89(3H,s), 2.54–0.8(4H,m).

EXAMPLE 40

Preparation of (±)-cis-7-[2-(2-amino-4-thiazolyl)-2-syn-methoxyiminoacetamido]-1-azabicyclo[4,2,0]oct-2-en-8-on-2-carboxylic acid:

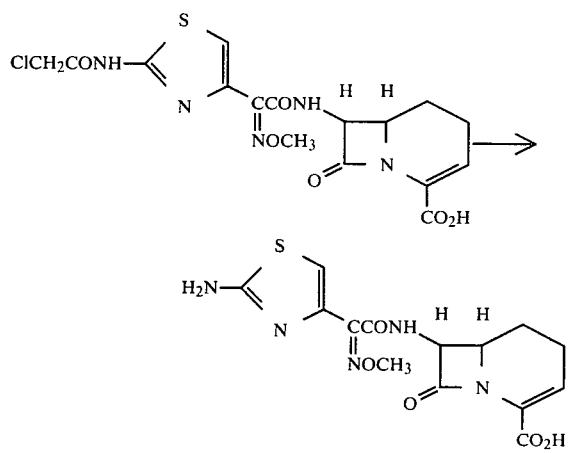

In this Example, 80 mg. of the compound obtained in Example 39 is dissolved in 0.96 ml of dimethylacetamide. To the solution, 27.5 mg. of thiourea is added at room temperature with stirring and the mixture is stirred for 14 hours. After addition of ether, the supernatant is removed by decantation to obtain a red oily residue. The residue is purified by silica gel chromatography using Diaion HP-10 to obtain 19.2 mg. of the desired compound having the following properties:

IR(KBr)$\nu_{max}^{cm-1}$: 1760, 1670, 1630.

PMR(DMSO-d$_6$)δ9.26(1H,d,J=8.6 Hz), 7.11(2H,br), 6.75(1H,s), 6.30(1H,t), 5.47(1H,d-d,J=5.4, 8.8 Hz), 3.89(3H,s), 2.5–1.0(4H,m).

EXAMPLE 41

Preparation of (±)-cis-7β-(2-thienylacetamido)4α-acetoxy-1-azabicyclo[4,2,0]oct-2-en-8-on-2-carboxylic acid:

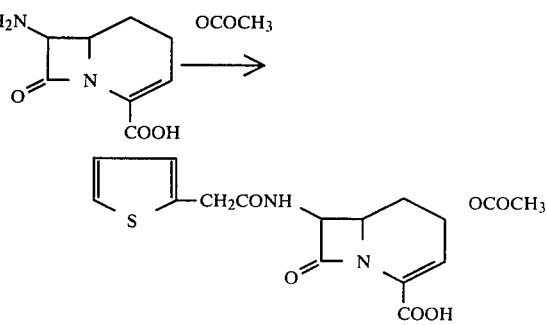

In this Example, 126 mg. of (±)-cis-7β-amino-4α-acetoxy-1-azabicyclo[4,2,0]oct-2-en-8-one-carboxylic acid obtained in Example 36 is dissolved in 3.0 ml of dioxane and 4.0 ml of water. The solution is cooled on an ice and sodium chloride bath. Then 105 mg. of sodium bicarbonate, and 84 mg. of 2-thienylacetylchloride dissolved in 1 ml of dioxane is added. The mixture is stirred for one hour. Then, the reaction mixture is adjusted to pH 2.0 with 1 N-hydrochloric acid and extracted three times with ethyl acetate. The extracts are combined and washed with saturated sodium chloride solution. The washing is dried with anhydrous sodium sulfate and is subjected to filtration. The filtrate is concentrated and the concentrate is charged on a column packed with 20 g of silica gel. Elution is carried out with a mixture of chloroform and ethanol (20:1, by volume). The fractions containing the desired compound are combined and concentrated to dryness to obtain 89.1 mg. of the desired compound as a pale yellow powder having the following properties. Yield 47%.

IR(KBr)$\nu_{max}^{cm-1}$: 1780, 1745, 1660.

NMR(CDCl$_3$+CD$_3$OD)$\delta$(ppm): 7.27–6.93(3H,m), 6.39(1H,d, J=5.4 Hz), 5.43(1H,d,J=4.9 Hz), 5.40(1H,m), 3.79(2H,s), 2.10–1.26(2H,m), 2.06(3H,s).

The antibacterial activity of the compounds obtained in the above Examples 24, 26, 28, 30, 32, 34, 36, 38, 40 and 41 are determined by Heart Infusion Agar Dilution Method (pH 7.2). The results are shown in the following table. Cefazolin is used as a reference.

In this Example, 54.0 mg (0.19 mmole) of ($\pm$)-cis-7$\beta$-azido-4$\alpha$-hydroxy-2-t-butyloxycarbonyl-1-azabicyclo[4, 2, 0] oct-2-en-8-one obtained in Example 17 is dissolved in 20 ml of ethanol and 15 mg of 10% palladium-carbon is added. The mixture is stirred in a stream of hydrogen at atmospheric pressure and room temperature for 1.5 hours. The reaction mixture is filtered to remove the catalyst and the filtrate is concentrated. The concentrate is subjected to silica gel chromatography [5 g of silica gel, a mixture of chloroform and methanol (4:1)]. Thus, 21.7 mg of the desired compound is obtained as a yellow glass. Yield 44.3%.

IR(CHCl$_3$)$\nu_{max}^{cm-1}$: 3250–3400, 1775, 1730, 1635.

NMR(CDCl$_3$)$\delta$(ppm): 6.28(1H, d, J=6.0), 4.62(1H, d, J=5.0), 4.47(1H, m), 4.50–3.30(1H, m), 2.52(3H, br), 2.50–1.50(2H, m), 1.53(9H, s).

What is claimed is:

1. A process for producing compounds represented by the formula

| Micro-organism | Minimum Inhibitory Concentration (μg/ml) | | | | | | | | | | | | Cefazolin |
|---|---|---|---|---|---|---|---|---|---|---|---|---|---|
| | a | b | c | d | e | f | g | h | i | j | k | l | |
| 1 | 100 | 0.4 | — | 0.4 | 0.78 | 0.4 | 0.78 | 12.5 | 50 | 12.5 | 12.5 | 3.12 | <0.05 |
| 2 | >100 | 12.5 | — | 6.25 | 3.12 | 1.56 | 6.25 | 25 | 100 | 12.5 | 12.5 | 25 | 0.4 |
| 3 | 100 | 6.25 | — | 3.12 | 3.12 | 3.12 | 6.25 | 25 | >100 | 12.5 | 12.5 | 12.5 | 0.78 |
| 4 | 0.78 | 12.5 | 50 | 3.12 | 1.56 | 50 | 12.5 | 0.4 | 0.2 | ≦0.05 | ≦0.05 | 100 | 1.56 |
| 5 | 1.56 | 12.5 | 100 | 3.12 | 1.56 | 25 | 12.5 | 0.78 | 1.56 | ≦0.05 | ≦0.05 | 100 | 1.56 |
| 6 | 0.2 | 3.12 | 50 | 0.78 | <0.05 | 6.25 | 3.12 | 0.1 | 0.2 | ≦0.05 | ≦0.05 | >100 | 0.78 |
| 7 | 1.56 | 12.5 | 50 | 3.12 | 25 | 100 | >100 | 1.56 | 1.56 | ≦0.05 | ≦0.05 | 25 | 3.12 |
| 8 | 3.12 | >100 | — | — | 25 | >100 | >100 | 25 | 6.25 | 1.56 | 0.78 | >100 | >100 |
| 9 | 1.56 | 25 | 100 | 12.5 | 3.12 | >100 | 25 | 1.56 | 3.12 | 0.1 | ≦0.05 | >100 | 50 |
| 10 | 0.78 | 25 | 25 | 12.5 | 1.56 | >100 | 50 | 0.2 | 0.78 | ≦0.05 | ≦0.05 | >100 | 12.5 |
| 11 | 0.4 | 25 | 25 | 50 | <0.05 | >100 | 50 | <0.05 | 0.78 | ≦0.05 | ≦0.05 | >100 | 12.5 |
| 12 | 0.78 | 100 | 50 | 50 | 3.12 | >100 | 100 | 0.78 | 0.78 | ≦0.05 | ≦0.05 | >100 | >100 |
| 13 | 0.1 | 50 | 6.25 | 12.5 | 6.25 | >100 | >100 | 0.1 | 0.4 | ≦0.05 | ≦0.05 | >100 | 25 |
| 14 | >100 | >100 | — | — | 100 | >100 | >100 | >100 | >100 | >100 | 50 | >100 | >100 |
| 15 | 0.78 | >100 | — | 100 | 6.25 | >100 | 100 | 1.56 | 0.4 | ≦0.05 | 0.1 | >100 | >100 |

1 : *Staphylococcus aureus* 209-p
2 : *Staphylococcus aureus* Smith
3 : *Staphylococcus epidermidis*
4 : *Escherichia coli* NIHJC-2
5 : *Escherichia coli* Juhl
6 : *Klebsiella pneumoniae* 8045
7 : *Klebsiella pneumoniae* Y-60
8 : *Serratia marcescens* T-26
9 : *Serratia marcescens* T-55
10 : *Proteus mirabilis* 1287
11 : *Proteus vulgaris* 6897
12 : *Proteus morganii* KY4298
13 : *Proteus rettgeri* KY4289
14 : *Pseudomonas aeruginosa* 145
15 : *Pseudomonas putida* F264
a : The compound obtained in Example 24
b : The compound obtained in Example 26
c : A isomer obtained in Example 26
d : B isomer obtained in Example 26
e : The compound obtained in Example 28
f : The compound obtained in Example 30
g : The compound obtained in Example 32
h : The compound obtained in Example 34
i : The compound obtained in Example 36
j : The compound obtained in Example 38
k : The compound obtained in Example 40
l : The compound obtained in Example 41

EXAMPLE 42

Preparation of ($\pm$)-cis-7$\beta$-amino-4$\alpha$-hydroxy-2-t-butyloxycarbonyl-1-azabicyclo[4,2,0]oct-2-en-8-one wherein R$_1$ represents a hydrogen atom, a halo group, a hydroxy group, a lower alkoxy group having 1 to 5 carbon atoms, a lower alkylthio group having 1 to 5 carbon atoms, a phenylthio group, a benzylthio group, a lower alkylsulfinyl group corresponding to the alkylthio group described above, a lower alkylsulfonyl group corresponding to the alkylthio group described above, a phenylsulfonyl group corresponding to the phenylthio group described above, or a benzylsulfonyl group corresponding to the benzylthio group described above, $R_2$ is a group as defined for $R_1$ or represents an alkanoyl group, a lower alkyl group having 1 to 5 carbon atoms, a lower alkyl group having 1 to 5 carbon atoms and substituted with a halo group, a nitrile group or an amino group represented by the formula $NR_9R_{10}$ wherein $R_9$ and $R_{10}$ may be the same or different and represent a hydrogen atom, a lower aklyl group having 1 to 5 carbon atoms, a phenyl group, or a benzyl group, wherein the alkyl group in $R_1$ and $R_2$ is a straight-chain alkyl group, and $R_3$ represents a hydrogen atom or a substituted or unsubstituted alkyl, aryl, aralkyl or silyl group selected from methyl group, ethyl group, n-propyl group, isopropyl group, n-butyl group, isobutyl group, t-butyl group, a chloromethyl group, 2,2,2-trichloroethyl group, 2,2,2-trifluoroethyl group, benzyl group, diphenylmethyl group, triphenylmethyl group, trimethylsilyl group and triphenylsilyl group, among which benzyl group, diphenylmethyl group and triphenylmethyl group may have a methoxy or nitro group on the phenyl group, and acid addition salts thereof, wherein an $X_1$ group of the compound represented by the formula wherein $X_1$ represents an azido group and $R_1$, $R_2$ and $R_3$ have the same significance as defined above is reduced by catalytic reduction to an amino group using pallidium on charcoal, Raney nickel, palladium black or platinum oxide at a temperature of 0° to 100° C. and at a pressure of 1 to 50 atmospheres.

2. The process of claim 1, wherein $R_1$ and $R_2$ are a hydrogen atom and $R_3$ is a t-butyl group or a hydrogen group.

3. The process of claim 1, wherein $R_1$ is a hydrogen atom, $R_2$ is a methyl group, a halo group, hydroxy group or acetoxy group and $R_3$ is a t-butyl group or hydrogen group.

* * * * *

UNITED STATES PATENT AND TRADEMARK OFFICE
CERTIFICATE OF CORRECTION

PATENT NO. : 4,291,164
DATED : September 22, 1981
INVENTOR(S) : HIRATA, et al.

It is certified that error appears in the above—identified patent and that said Letters Patent is hereby corrected as shown below:

Col. 1, line 11, "(177)" should read --(1977)--.

Col. 3, line 22, after "as" insert --a--.

Col. 4, line 24, "2,2,2-tetrafluorethyl" should read --2,2,2-trifluoroethyl--.

Col. 10, line 67, "[IX]" should read --[XI]--.

Col. 11, line 16, "[XIII]" should read --[XII]--.

Col. 14, line 68, "$R_2$" should read --$R_{21}$--.

Col. 16, line 32, "methachlorobenzoic" should read --metachlorobenzoic--.

Col. 19, line 68, "amine salt" should read --amine salts--.

UNITED STATES PATENT AND TRADEMARK OFFICE
CERTIFICATE OF CORRECTION

PATENT NO. : 4,291,164
DATED : September 22, 1981
INVENTOR(S) : HIRATA, et al.

It is certified that error appears in the above—identified patent and that said Letters Patent is hereby corrected as shown below:

Col. 20, lines 13 - 20, the formula should read

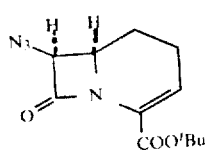

Col. 21, line 24, "-en-8one" should read -- -en-8-one--.

UNITED STATES PATENT AND TRADEMARK OFFICE
CERTIFICATE OF CORRECTION

PATENT NO. : 4,291,164
DATED : September 22, 1981
INVENTOR(S) : HIRATA, et al.

It is certified that error appears in the above—identified patent and that said Letters Patent is hereby corrected as shown below:

Col. 22, lines 13 - 20, the formula should read

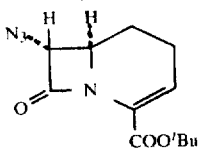

Col. 23, lines 3 - 10, the formula should read

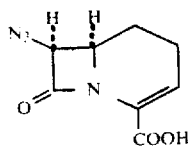

Col. 23, lines 36 - 43, the formula should read

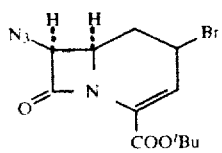

Col. 24, lines 10 - 17, the formula should read

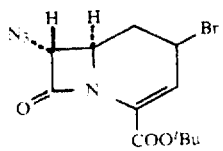

UNITED STATES PATENT AND TRADEMARK OFFICE
CERTIFICATE OF CORRECTION

PATENT NO. : 4,291,164

DATED : September 22, 1981

INVENTOR(S) : HIRATA, et al.

It is certified that error appears in the above—identified patent and that said Letters Patent is hereby corrected as shown below:

Col. 24, lines 51 - 58, the formula should read

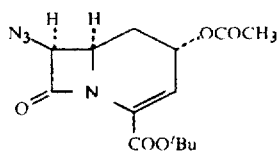

Col. 25, lines 23 - 30; Col. 26, lines 35 - 42 and Col. 32, lines 8 - 15, the formula should read

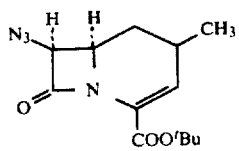

Col. 27, lines 36 - 43, and Col. 29, lines 25 - 33, the formula should be

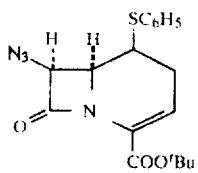

Col. 28, line 34 "(4H,g)" should read --(4H,q)--.

Col. 29, line 21, "-en-8one" should read -- -en-8-one--.

Col. 29, line 64, "(1H,d-d-d,=3," should read --(1H,d-d-d, J=3,--.

Col. 30, line 42, "-2-butyloxycarbonyl-" should read -- -2-t-butyloxycarbonyl--.

UNITED STATES PATENT AND TRADEMARK OFFICE
CERTIFICATE OF CORRECTION

PATENT NO. : 4,291,164

DATED : September 22, 1981

INVENTOR(S) : HIRATA, et al.

It is certified that error appears in the above—identified patent and that said Letters Patent is hereby corrected as shown below:

Col. 30, lines 55 - 65, the formula should read

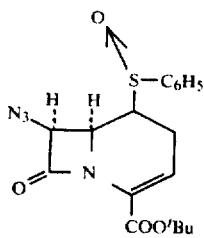

Col. 31, lines 50 - 57, the formulae should read

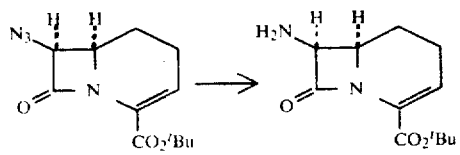

Col. 34, lines 1 - 9, the formulae should read

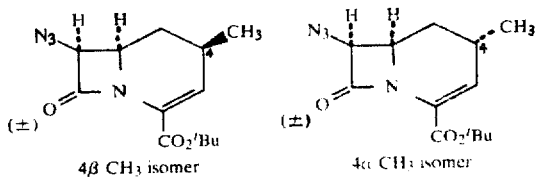

4β CH₃ isomer    4α CH₃ isomer

Col. 34, lines 29 - 36, the formulae should read

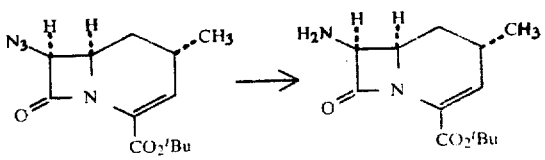

UNITED STATES PATENT AND TRADEMARK OFFICE
CERTIFICATE OF CORRECTION

PATENT NO. : 4,291,164
DATED : September 22, 1981
INVENTOR(S) : HIRATA, et al.

It is certified that error appears in the above—identified patent and that said Letters Patent is hereby corrected as shown below:

Col. 35, lines 1 - 9, the formulae should read

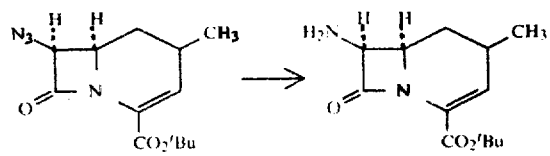

Col. 35, lines 32 - 44, the formulae should read

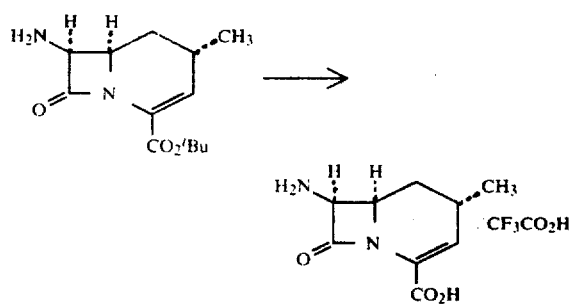

UNITED STATES PATENT AND TRADEMARK OFFICE
CERTIFICATE OF CORRECTION

PATENT NO. : 4,291,164
DATED : September 22, 1981
INVENTOR(S) : HIRATA, et al.

Page 7 of 15

It is certified that error appears in the above—identified patent and that said Letters Patent is hereby corrected as shown below:

Col. 36, lines 1 - 14, the formulae should read

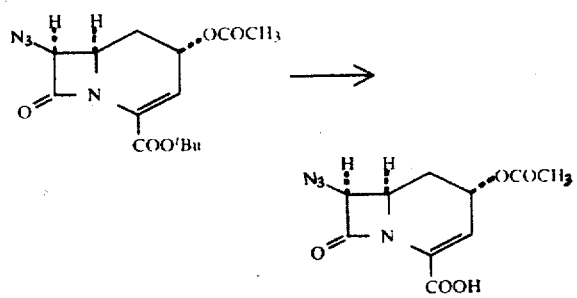

Col. 36, lines 24 - 38, the formulae should read

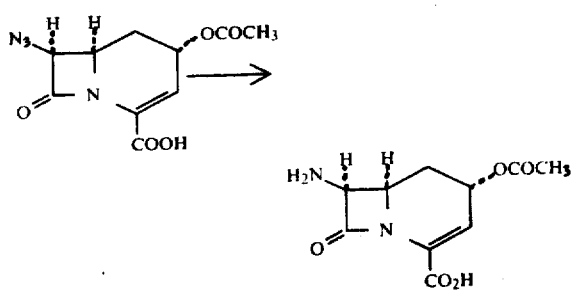

Col. 36, lines 56 - 63, the formula should read

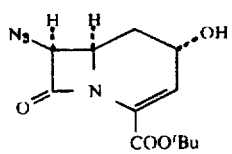

UNITED STATES PATENT AND TRADEMARK OFFICE
CERTIFICATE OF CORRECTION

PATENT NO. : 4,291,164

DATED : September 22, 1981

INVENTOR(S) : HIRATA, et al.

It is certified that error appears in the above—identified patent and that said Letters Patent is hereby corrected as shown below:

Col. 37, lines 57 - 64, the formulae should read

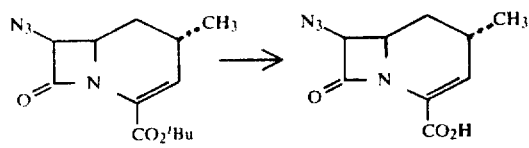

Col. 38, lines 30 - 43, the formulae should read

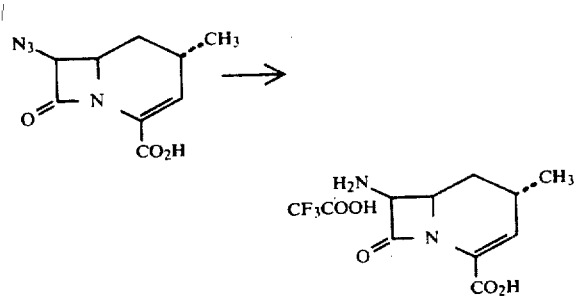

Col. 41, line 22, "-2t-butyloxycarbonyl-" should read
-- -2-t-butyloxycarbonyl- --.

Col. 41, line 44, "-cis-[(R)-2-" should read
-- -cis-7-[(R)-2- --.

Col. 43, line 19, "en-8-one-" should read --en-8-on- --.

UNITED STATES PATENT AND TRADEMARK OFFICE
CERTIFICATE OF CORRECTION

PATENT NO. : 4,291,164
DATED : September 22, 1981
INVENTOR(S) : HIRATA, et al.

It is certified that error appears in the above—identified patent and that said Letters Patent is hereby corrected as shown below:

Col. 46, lines 7 - 20, the formulae should read

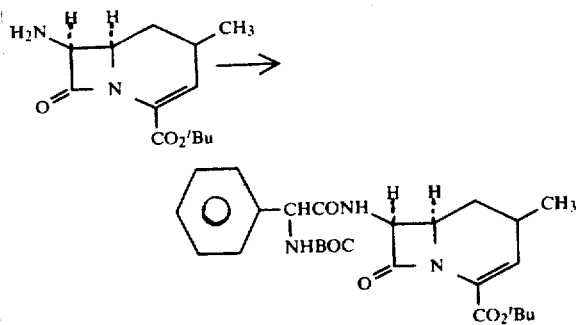

Col. 46, lines 60 - 68, the formula should read

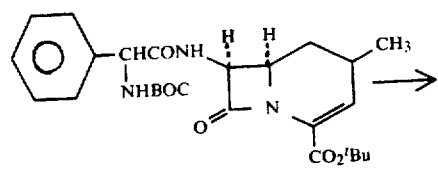

Col. 47, lines 1 - 10, the formula should read

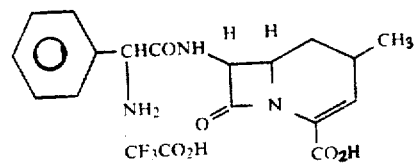

UNITED STATES PATENT AND TRADEMARK OFFICE
CERTIFICATE OF CORRECTION

PATENT NO. : 4,291,164

DATED : September 22, 1981

INVENTOR(S) : HIRATA, et al.

It is certified that error appears in the above—identified patent and that said Letters Patent is hereby corrected as shown below:

Col. 47, lines 40 - 54, the formulae should read

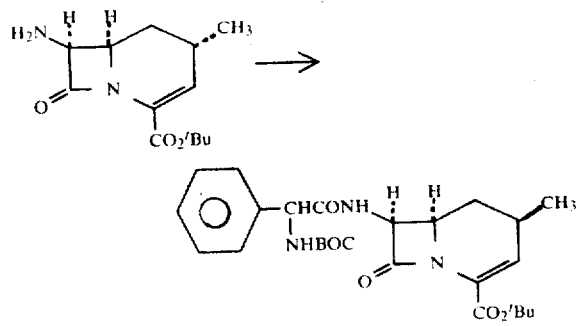

Col. 48, lines 6 - 22, the formulae should be

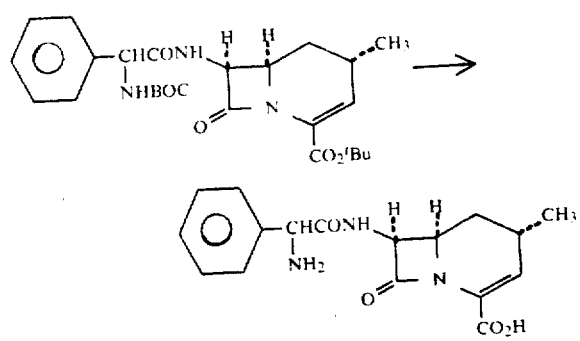

UNITED STATES PATENT AND TRADEMARK OFFICE
CERTIFICATE OF CORRECTION

PATENT NO. : 4,291,164
DATED : September 22, 1981
INVENTOR(S) : HIRATA, et al.

It is certified that error appears in the above—identified patent and that said Letters Patent is hereby corrected as shown below:

Col. 48, lines 42 - 56, the formulae should read

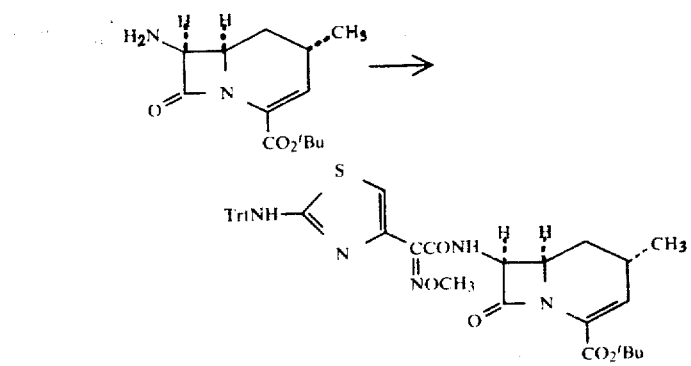

Col. 49, lines 60 - 68, the formula should read

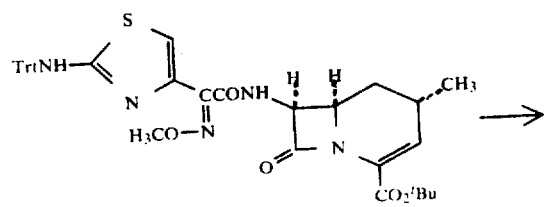

Col. 50, lines 3 - 10, the formula should read

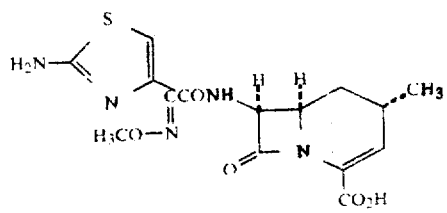

UNITED STATES PATENT AND TRADEMARK OFFICE
CERTIFICATE OF CORRECTION

PATENT NO. : 4,291,164

DATED : September 22, 1981

INVENTOR(S) : HIRATA, et al.

It is certified that error appears in the above—identified patent and that said Letters Patent is hereby corrected as shown below:

Col. 50, lines 45 - 60, the formulae should read

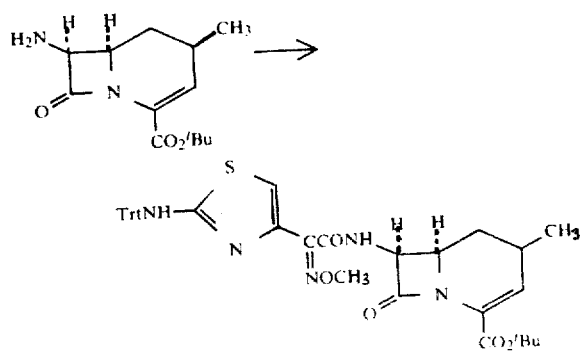

Col. 51, lines 14 - 30, the formulae should read

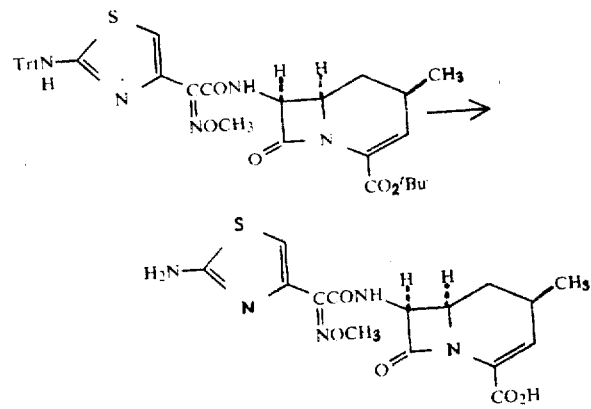

UNITED STATES PATENT AND TRADEMARK OFFICE
CERTIFICATE OF CORRECTION

PATENT NO. : 4,291,164

DATED : September 22, 1981

INVENTOR(S) : HIRATA, et al.

Page 13 of 15

It is certified that error appears in the above—identified patent and that said Letters Patent is hereby corrected as shown below:

Col. 51, lines 51 - 65, the formulae should read

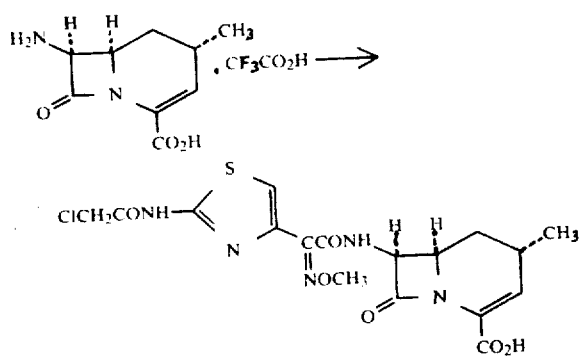

Col. 52, lines 37 - 54, the formulae should read

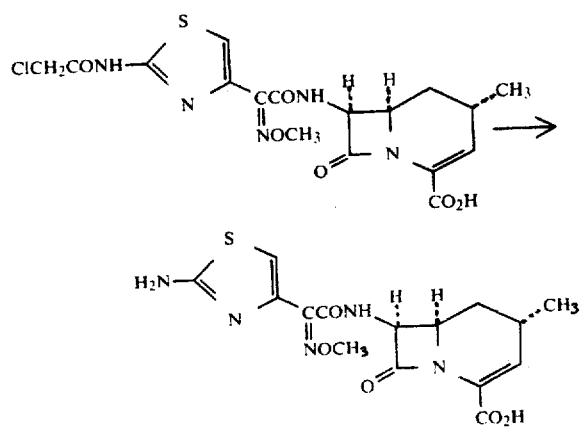

UNITED STATES PATENT AND TRADEMARK OFFICE
CERTIFICATE OF CORRECTION

PATENT NO. : 4,291,164
DATED : September 22, 1981
INVENTOR(S) : Hirata

It is certified that error appears in the above—identified patent and that said Letters Patent is hereby corrected as shown below:

Col. 53, lines 20 - 35, the formulae should read

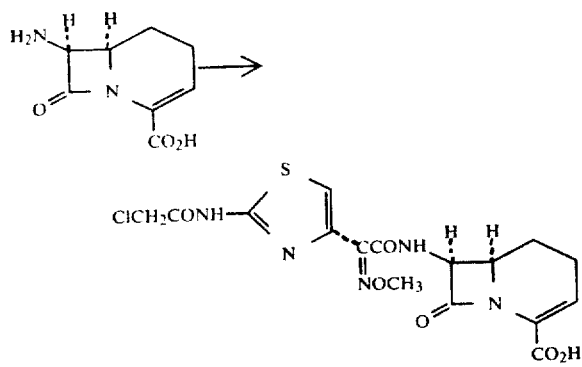

Col. 54, lines 6 - 24, the formulae should read

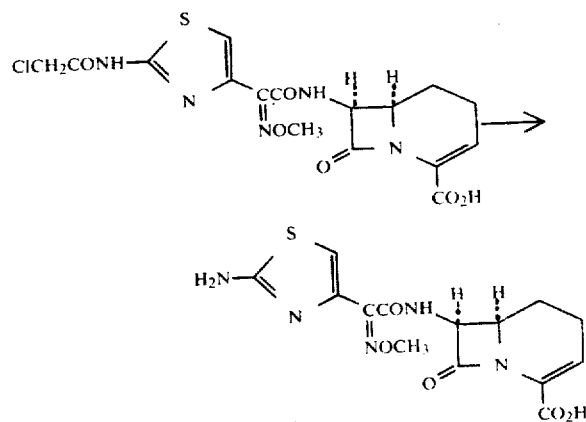

UNITED STATES PATENT AND TRADEMARK OFFICE
CERTIFICATE OF CORRECTION

PATENT NO. : 4,291,164

DATED : September 22, 1981

INVENTOR(S) : HIRATA, et al.

It is certified that error appears in the above—identified patent and that said Letters Patent is hereby corrected as shown below:

Col. 54, lines 43 - 57, the formulae should read

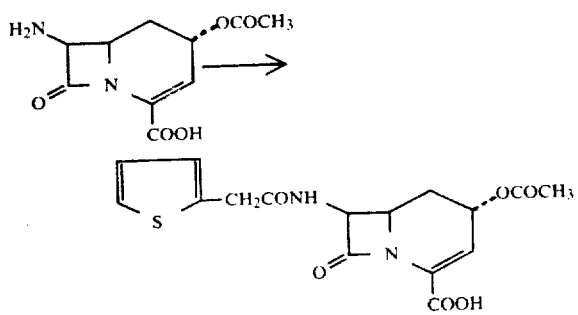

Col. 55, lines 61 - 68, the formula should read

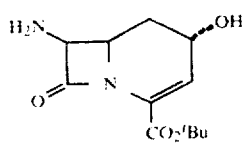

Signed and Sealed this

Eleventh Day of May 1982

[SEAL]

Attest:

GERALD J. MOSSINGHOFF

Attesting Officer    Commissioner of Patents and Trademarks